US008715973B1

(12) United States Patent
Pfleger et al.

(10) Patent No.: US 8,715,973 B1
(45) Date of Patent: May 6, 2014

(54) ORGANIC ACID-TOLERANT MICROORGANISMS AND USES THEREOF FOR PRODUCING ORGANIC ACIDS

(71) Applicant: Wisconsin Alumni Research Foundation, Madison, WI (US)

(72) Inventors: Brian Frederick Pfleger, Madison, WI (US); Matthew Brett Begemann, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/798,835

(22) Filed: Mar. 13, 2013

Related U.S. Application Data

(60) Provisional application No. 61/647,001, filed on May 15, 2012.

(51) Int. Cl.
*C12P 7/52* (2006.01)
*C12P 7/40* (2006.01)
*C12P 7/04* (2006.01)
*C12N 9/88* (2006.01)
*C12P 7/42* (2006.01)

(52) U.S. Cl.
USPC .......................... 435/141; 435/132; 435/136

(58) Field of Classification Search
None
See application file for complete search history.

(56) References Cited

U.S. PATENT DOCUMENTS

| 8,048,624 | B1 | 11/2011 | Lynch |
| 2010/0210017 | A1 | 8/2010 | Gill |
| 2011/0125118 | A1 | 5/2011 | Lynch |
| 2011/0165637 | A1 | 7/2011 | Pfleger et al. |

OTHER PUBLICATIONS

Altschul et al., Basic Local Alignment Search Tool, *J. Mol. Biol.* 1990, 215:403-410.
Angermayr et al., Energy biotechnology with cyanobacteria. *Current Opinion in Biotechnology*, 2009, 20(3): p. 257-263.
Ansede et al., Metabolism of Acrylate to beta—Hydroxypropionate and Its Role in Dimethylsulfoniopropionate Lyase Induction by a Salt Marsh Sediment Bacterium, *Alcaligenes faecalis* M3A. *Appl. Environ. Microbiol.*, 1999. 65(11): p. 5075-5081.
Atsumi et al., Direct photosynthetic recycling of carbon dioxide to isobutyraldehyde. *Nat Biotech*, 2009, 27(12): p. 1177-1180.
Balasubramanian et al., Regulatory Roles for IscA and SufA in Iron Homeostasis and Redox Stress Responses in the Cyanobacterium *Synechococcus* sp. Strain PCC 7002. *J. Bacteriol.*, 2006, 188(9): p. 3182-3191.
Bauer, W., Acrylic Acid and Derivatives. *Kirk-Othmer Encyclopedia of Chemical Technology*. 2000: John Wiley & Sons, Inc.
Boynton et al., Intracellular Concentrations of Coenzyme A and Its Derivatives from Clostridium acetobutylicum ATCC 824 and Their Roles in Enzyme Regulation. *Appl. Environ. Microbiol.*, 1994, 60(1): p. 39-44.
Bozell et al., Technology development for the production of biobased products from biorefinery carbohydrates—the US Department of Energy's "Top 10" revisited. *Green Chemistry*, 2010, 12(4): p. 539-554.
Cherrington et al., Organic Acids: Chemistry, Antibacterial Activity and Practical Applications, in Advances in Microbial Physiology, A.H. Rose and D.W. Tempest, Editors. 1991, *Academic Press.* p. 87-108.
Chotani et al., The commercial production of chemicals using pathway engineering. *Biochimica et Biophysica Acta (BBA)—Protein Structure and Molecular Enzymology*, 2000, 1543(2): p. 434-455.
Current Protocols in Molecular Biology, F.M. Ausubel et al., eds., Current Protocols, a joint venture between Greene Publishing Associates, Inc. and John Wiley & Sons, Inc., (supplemented through 2008.
Dacey et al., Hydroxide decomposition of dimethylsulfoniopropionate to form dimethylsulfide. *Geophys. Res. Lett.* 1987, 14:1246-1249.
Ducat et al., Engineering cyanobacteria to generate high-value products. *Trends in Biotechnology*, 2011, 29(2): p. 95-103.
Feist et al., Reconstruction of biochemical networks in microorganisms. *Nat Rev Micro*, 2009, 7(2): p. 129-143.
Fridovich et al., Paraquat and the exacerbation of oxygen toxicity. *Trends in Biochemical Sciences*, 1979, 4(5): p. 113-115.
González et al., Genetics and Molecular Features of Bacterial Dimethylsulfoniopropionate (DMSP) and Dimethylsulfide (DMS) Transformations, in *Handbook of Hydrocarbon and Lipid Microbiology*, K.N. Timmis, Editor. 2010, Springer Berlin Heidelberg. p. 1201-1211.
Green et al., Molecular Cloning: A laboratory Manual, 4$^{th}$ ed., Cold Spring Harbor Laboratory Press, 2001.
Hashimoto et al., Nitrile Pathway Involving Acyl-CoA Synthetase. *Journal of Biological Chemistry*, 2005, 280(10): p. 8660-8667.
Henikoff & Henikoff, Amino acid substitution matrices from protein blocks, *Proc. Natl. Acad. Sci. USA*, 1989, 89:10915.
Holo, H., *Chloroflexus aurantiacus* secretes 3-hydroxypropionate, a possible intermediate in the assimilation of $CO^2$ and acetate. Archives of Microbiology, 1989, 151(3): p. 252-256.

(Continued)

*Primary Examiner* — John S Brusca
*Assistant Examiner* — Gerard Lacourciere
(74) *Attorney, Agent, or Firm* — Daniel A. Blasiole; Joseph T. Leone, Esq.; DeWitt, Ross, & Stevens S.C.

(57) ABSTRACT

Organic acid-tolerant microorganisms and methods of using same. The organic acid-tolerant microorganisms comprise modifications that reduce or ablate AcsA activity or AcsA homolog activity. The modifications increase tolerance of the microorganisms to such organic acids as 3-hydroxypropionic acid (3HP), acrylic acid, and propionic acid. Further modifications to the microorganisms such as increasing expression of malonyl-CoA reductase and/or acetyl-CoA carboxylase provide or increase the ability of the microorganisms to produce 3HP. Methods of generating an organic acid with the modified microorganisms are provided. Methods of using acsA or homologs thereof as counter-selectable markers include replacing acsA or homologs thereof in cells with genes of interest and selecting for the cells comprising the genes of interest with amounts of organic acids effective to inhibit growth of cells harboring acsA or the homologs.

19 Claims, 8 Drawing Sheets

(56) References Cited

OTHER PUBLICATIONS

Horswill et al., Studies of Propionate Toxicity in *Salmonella enterica* Identify 2-Methylcitrate as a Potent Inhibitor of Cell Growth. *Journal of Biological Chemistry*, 2001, 276(22): p. 19094-19101.
Howard, E.C., et al., *Bacterial Taxa That Limit Sulfur Flux from the Ocean. Science*, 2006. 314(5799): p. 649-652.
Howard et al., Abundant and diverse bacteria involved in DMSP degradation in marine surface waters. *Environmental Microbiology*, 2008, 10(9): p. 2397-2410.
Hugler et al., Malonyl-Coenzyme A Reductase from Chloroflexus aurantiacus, a Key Enzyme of the 3-Hydroxypropionate Cycle for Autotrophic $CO_2$ Fixation. *J. Bacteriol.*, 2002, 184(9): p. 2404-2410.
Karlin et al., Application and statistics for multiple high-scoring segments in molecular sequences, *Proc. Natl. Acad. Sci. USA*, 1993, 90:5873-5787.
Kasuya et al.,, Participation of a medium chain acyl-CoA synthetase in glycine conjugation of the benzoic acid derivatives with the electron-donating groups. *Biochemical Pharmacology*, 1996, 51(6): p. 805-809.
Keasling, J.D., *Manufacturing Molecules Through Metabolic Engineering. Science*, 2010, 330(6009): p. 1355-1358.
Kiene et al., Dimethylsulfoniopropionate and Methanethiol Are Important Precursors of Methionine and Protein-Sulfur in Marine Bacterioplankton. *Appl. Environ. Microbiol.*, 1999, 65(10): p. 4549-4558.
Kumar et al., Development of suitable photobioreactors for $CO_2$ sequestration addressing global warming using green algae and cyanobacteria. *Bioresource Technology*, 2011, 102(8): p. 4945-4953.
Latifi et al., Oxidative stress in cyanobacteria. *FEMS Microbiology Reviews*, 2009, 33(2): p. 258-278.
Lindberg et al.,, Engineering a platform for photosynthetic isoprene production in cyanobacteria, using Synechocystis as the model organism. *Metabolic Engineering*, 2010, 12(1): p. 70-79.
Liu et al., Fatty acid production in genetically modified cyanobacteria. Proceedings of the National Academy of Sciences, 2011.
Malmstrom et al., Dimethylsulfoniopropionate (DMSP) Assimilation by *Synechococcus* in the Gulf of Mexico and Northwest Atlantic Ocean. *Limnology and Oceanography*, 2005, 50(6): p. 1924-1931.
Man et al., the binding of propionyl-CoA and carboxymethyl-CoA to *Escherichia coli* citrate synthase. *Biochimica et Biophysica Acta (BBA)—Protein Structure and Molecular Enzymology*, 1995, 1250(1): p. 69-75.
Maruyama et al., Mechanisms of Growth Inhibition by Propionate and Restoration of the Growth by Sodium Bicarbonate or Acetate in *Rhodopseudomonas sphaeroides* S. *Journal of Biochemistry*, 1985, 98(3): p. 819-824.
Nakamura et al, Metabolic engineering for the microbial production of 1,3-propanediol. *Current Opinion in Biotechnology*, 2003, 14(5): p. 454-459.
Needleman et al., A General Method Applicable to the Search for Similarities in the Amino Acid Sequence of Two Proteins, *J. Mol. Biol.* 1970, 48:443.
Niederholtmeyer et al., Engineering Cyanobacteria to Synthesize and Export Hydrophilic Products. *Appl. Environ. Microbiol.*, 2010, 76(11): p. 3462-3466.
Olins et al., A Novel Sequence Element Derived from Bacteriophage T7 mRNA Acts as an Enhancer of Translation of the *lacZ* Gene in *Escherichia coli, Journal of Biological Chemistry*, 1989, 264(29):16973-16976.
*OPX nears commercial goal for bio-based acrylic acid* Feb. 28, 2011; Available from: http://www.opxbio.com/news/opxbio-rapidly-achieves-bioacrylic-commercial-goals/.
Pearson et al., Improved tools for biological sequence comparison, *Proc. Nat'l. Acad. Sci. USA*, 1988, 85:2444.
Reisch et al., Novel pathway for assimilation of dimethylsulphoniopropionate widespread in marine bacteria. *Nature*, 2011, 473(7346): p. 208-211.
Riddles et al., Ellman's reagent: 5,5'-dithiobis(2-nitrobenzoic acid)-a reexamination, *Analytical Biochemistry*, 1979, 94(1):75-81.
Ross et al., Intraspecific Variation in Stress-Induced Hydrogen Peroxide Scavenging by The Ulvoid Macroalga Ulva Lactucal. *Journal of Phycology*, 2007, 43(3): p. 466-474.
Russell, J.B., Another explanation for the toxicity of fermentation acids at low pH: anion accumulation versus uncoupling. *Journal of Applied Microbiology*, 1992, 73(5): p. 363-370.
Sakamoto et al.,, Growth on Urea Can Trigger Death and Peroxidation of the Cyanobacterium *Synechococcus* sp. Strain PCC 7002. *Appl. Environ. Microbiol.*, 1998, 64(7): p. 2361-2366.
Sambrook et al., *Molecular cloning: A Laboratory Manual*, $3^{rd}$ ed., Cold Spring Harbor Laboratory Press, 2001.
Simó, R., Production of atmospheric sulfur by oceanic plankton: biogeochemical, ecological and evolutionary links. *Trends in Ecology & Evolution*, 2001, 16(6): p. 287-294.
Simó et al., Coupled Dynamics of Dimethylsulfoniopropionate and Dimethylsulfide Cycling and the Microbial Food Web in Surface Waters of the North Atlantic. *Limnology and Oceanography*, 2002, 47(1): p. 53-61.
Smith et al., Comparison of Biosequences, *Adv. Appl. Math.* 1981, 2:482-489.
Steinke et al., Determinations of dimethylsulphoniopropionate (DMSP) lyase activity using headspace analysis of dimethylsulphide (DMS). *Journal of Sea Research*, 2000. 43(3-4): p. 233-244.
Straathof, A.J.J., et al., Feasibility of acrylic acid production by fermentation. *Applied Microbiology and Biotechnology*, 2005.67(6): p. 727-734.
Stefels, J., Physiological aspects of the production and conversion of DMSP in marine algae and higher plants. *Journal of Sea Research*, 2000, 43(3-4): p. 183-197.
Sunda et al., An antioxidant function for DMSP and DMS in marine algae. *Nature*, 2002, 418(6895): p. 317-320.
Thiel, T., Genetic Analysis of Cyanobacteria, in The Molecular Biology of Cyanobacteria, D.A. Bryant, Editor. 2004, Springer Netherlands. p. 581-611.
Vila-Costa et al., Dimethylsulfoniopropionate Uptake by Marine Phytoplankton. Science, 2006, 314(5799): p. 652-654.
Visscher et al., Production and Consumption of Dimethylsulfoniopropionate in Marine Microbial Mats. *Applied and Environmental Microbiology*, 1991, 57:3237-3242.
Warnecke et al., Rapid dissection of a complex phenotype through genomic-scale mapping of fitness altering genes, *Metabolic Engineering*, 2010, 12:241-250.
Xu et al., Expression of Genes in Cyanobacteria: Adaptation of Endogenous Plasmids as Platforms for High-Level Gene Expression in <i>*Synechococcus*<i> sp. PCC 7002, in *Photosynthesis Research Protocols*, R. Carpentier, Editor. 2011, Humana Press. p. 273-293.
Yoch, D.C., Dimethylsulfoniopropionate: Its Sources, Role in the Marine Food Web, and Biological Degradation to Dimethylsulfide. *Appl. Environ. Microbiol.*, 2002, 68(12): p. 5804-5815.
Zaldivar et al., Effect of organic acids on the growth and fermentation of ethanologenic *Escherichia coli* LY01. *Biotechnology and Bioengineering; Journal* vol. 66; Journal Issue: 4; Other Information: PBD: 1999: p. Medium: X; Size: pp. 203-210.

ORGANIC ACID-TOLERANT MICROORGANISMS AND USES THEREOF FOR PRODUCING ORGANIC ACIDS

CROSS-REFERENCE TO RELATED APPLICATIONS

This application claims priority under 35 USC §119(e) to U.S. Provisional Patent Application 61/647,001 filed May 15, 2012, the entirety of which is incorporated herein by reference.

STATEMENT REGARDING FEDERALLY SPONSORED RESEARCH

This invention was made with government support under FA9550-11-1-0038 awarded by the USAF/AFOSR and DE-FC02-07ER64494 awarded by the US Department of Energy. The government has certain rights in the invention.

FIELD OF THE INVENTION

The present invention relates to organic acid-tolerant microorganisms and uses thereof for producing organic acids.

BACKGROUND

Production of industrially useful chemicals has conventionally focused on the use of petroleum-like compounds as starting materials. However, various factors have increased interest in the production of such chemicals through microorganism-mediated bioconversion of biomass and other renewable resources.

Accordingly, the U.S. Department of Energy (DOE) recently identified several "building block" chemicals to be produced via microorganism consumption of biomass. The identified chemicals include 1,4 succinic acid, fumaric and malic acids, 2,5 furan dicarboxylic acid, 3-hydroxypropionic acid (3HP), aspartic acid, glucaric acid, glutamic acid, itaconic acid, levulinic acid, 3-hydroxybutyrolactone, glycerol, sorbitol, and xylitol/arabinitol. These chemicals can be converted to high-value, bio-based chemicals or materials.

As an example, 3HP can be readily transformed into a variety of commodity chemicals such as acrylic acid, methyl acrylate, and 1,3-propanediol. These commodity chemicals represent a multi-billion dollar a year industry and are used in the production of plastics, coatings, and fibers. U.S. demand for acrylic acid in particular is growing, exceeding $1 \times 10^9$ kg/year. The current means of synthesizing acrylic acid include oxidation of propylene. A thermodynamically favorable pathway for microbial production of acrylic acid has not been identified.

One hurdle facing the microbial production of industrially useful chemicals is that many, including 3HP, are toxic to the microbes capable of producing them. Recently, efforts have been made not only to increase microbial output of the chemicals but also to increase microbial tolerance to the chemicals. Some of these efforts have focused on the production of 3HP in the heterotrophic microbe *Escherichia coli*. See, e.g., U.S. Pat. No. 8,048,624 to Lynch, U.S. Pub. 2011/0125118 to Lynch, U.S. Pub. 2010/0210017 to Gill et al., and Warnecke et al. *Metabolic Engineering* (2010) 12:241-250.

While focusing on chemical production in heterotrophic microorganisms is a valuable strategy, a potential problem is the availability of carbon and energy sources such as food-based commodities and/or sugars derived from lignocellulosic biomass. An attractive alternative is to use phototrophic microorganisms, such as cyanobacteria. These microorganisms can produce chemical products from $CO_2$ and light energy without relying on consumption of higher-value carbon sources that can be used for other purposes, such as producing food, fuel, or other certain chemicals.

There is a need for microorganisms capable of producing high yields of industrially useful chemicals and having increased tolerance against those chemicals. There is also a need for microorganisms that use non-food-based feedstock in such production.

SUMMARY OF THE INVENTION

The present invention addresses the aforementioned needs by providing microorganisms with increased tolerance to organic acids. The present invention also provides microorganisms genetically modified to produce organic acids. Methods of producing organic acids with the microorganisms described herein are also provided.

Some versions of the invention provide an organic acid-tolerant microorganism comprising a modification that reduces or ablates AcsA activity or AcsA homolog activity in the microorganism, wherein tolerance to an organic acid selected from the group consisting of 3-hydroxypropionic acid (3HP), acrylic acid, and propionic acid is increased compared to a corresponding microorganism not comprising the modification.

The modification is preferably a genetic modification. The genetic modification is preferably a genetic modification other than or in addition to one resulting in a W49L substitution in AcsA or a corresponding substitution in an AcsA homolog.

The microorganism is preferably a bacterium, more preferably a cyanobacterium, and most preferably a cyanobacterium selected from the group consisting of *Synechococcus* sp., *Prochlorococcus* sp., *Synechocystis* sp., and *Nostoc* sp.

The tolerance to the organic acid is preferably increased at least about 25-fold in the microorganism of the invention compared to the corresponding microorganism.

The tolerance to the organic acid may include a minimum inhibitory concentration (MIC) of at least about 10 mM to acrylic acid, an MIC of at least about 100 mM to 3HP, and an MIC of at least about 200 mM to propionic acid.

In preferred versions of the invention, the microorganism is capable of producing 3HP.

The microorganism may include at least one recombinant nucleic acid configured to overexpress a 3HP pathway enzyme. The at least one recombinant nucleic acid encoding the 3HP pathway enzyme may include a malonyl-CoA reductase gene, such as the malonyl-CoA reductase gene derived from *Chloroflexus aurantiacus*. The at least one recombinant nucleic acid encoding the 3HP pathway enzyme may additionally or alternatively include an acetyl-CoA carboxylase gene. The recombinant nucleic acids may be heterologous or may comprise heterologous elements.

Some versions of the invention provide a microbial culture comprising a microorganism as described herein and an amount of an organic acid. The amount of the organic acid may be selected from the group consisting of at least about 10 mM acrylic acid, at least about 100 mM 3HP, and at least about 200 mM propionic acid.

Further versions of the invention provide a method of producing an organic acid comprising culturing a microorganism as described herein in the presence of an amount of an organic acid. The organic acid may be selected from the group consisting of 3HP, acrylic acid, and propionic acid. The amount of the organic acid may be selected from the group consisting of at least about 10 mM acrylic acid, at least about 100 mM 3HP, and at least about 200 mM propionic acid.

Another version of the invention includes methods of using acsA or homolog thereof as a counter-selectable marker. One method includes replacing an acsA or homolog thereof in a cell with a gene of interest and selecting for the cell comprising the gene of interest with an amount of an organic acid effective to inhibit growth of cells harboring a functional acsA gene or homolog thereof. The replacing preferably occurs through homologous recombination. The acsA or homolog thereof is preferably an acsA gene with at least one silent nucleic acid mutation that reduces background mutation frequency. The at least one silent nucleic acid mutation is preferably selected from the group consisting of T144C and G150C in acsA from *Synechococcus* sp. PCC 7002. The organic acid is preferably acrylate. The cell may comprise any cell in which acsA or a homolog thereof confers sensitivity to organic acids. Such a cell may include a *Synechococcus* sp. cell or a cell from any microorganism described herein, known in the art, or later discovered that harbors an acsA homolog. The selecting preferably results in the cell being homozygous for the gene of interest.

The objects and advantages of the invention will appear more fully from the following detailed description of the preferred embodiment of the invention made in conjunction with the accompanying drawings.

DETAILED DESCRIPTION OF THE INVENTION

Figure 1A:
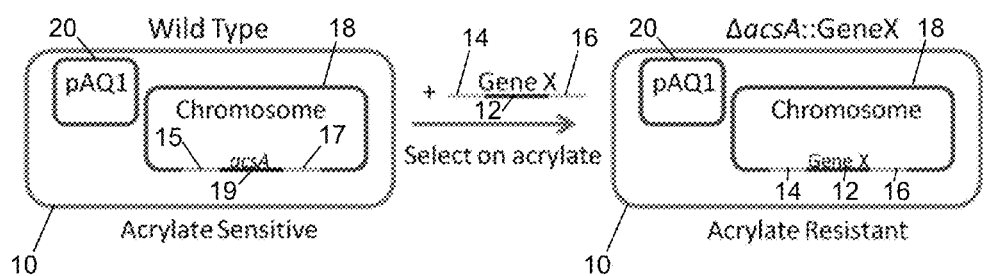
FIG. 1A depicts a schema for using acsA or a homolog thereof as a selection marker for introducing a DNA fragment of interest into the acsA or homolog chromosomal locus.

One version of the invention includes a microorganism wherein an acsA gene product or homolog thereof is functionally deleted. The acsA gene product (AcsA) and homologs thereof are acetyl-CoA synthetases classified under Enzyme Commission (EC) number 6.2.1.1. Other names for these acetyl-CoA synthetases include "acetate-CoA ligases," "acetyl-CoA ligases," and "acyl-activating enzymes."

"Functional deletion" or its grammatical equivalents refers to any modification to a microorganism that ablates, reduces, inhibits, or otherwise disrupts production of a gene product, renders the gene product non-functional, or otherwise reduces or ablates the gene product's activity. "Gene product" refers to a protein or polypeptide encoded and produced by a particular gene. In some versions of the invention, "functionally deleted acsA gene product or homolog thereof" means that the acsA gene is mutated to an extent that an acsA gene product or homolog thereof is not produced at all.

One of ordinary skill in the art will appreciate that there are many well-known ways to functionally delete a gene product. For example, functional deletion can be accomplished by introducing one or more genetic modifications. As used herein, "genetic modifications" refer to any differences in the nucleic acid composition of a cell, whether in the cell's native chromosome or in endogenous or exogenous non-chromosomal plasmids harbored within the cell. Examples of genetic modifications that may result in a functionally deleted gene product include but are not limited to mutations, partial or complete deletions, insertions, or other variations to a coding sequence or a sequence controlling the transcription or translation of a coding sequence; placing a coding sequence under the control of a less active promoter; and expressing ribozymes or antisense sequences that target the mRNA of the gene of interest, etc. In some versions, a gene or coding sequence can be replaced with a selection marker or screenable marker. Various methods for introducing the genetic modifications described above are well known in the art and include homologous recombination, among other mechanisms. See, e.g., Green et al., *Molecular Cloning: A laboratory manual*, 4th ed., Cold Spring Harbor Laboratory Press (2012) and Sambrook et al., *Molecular Cloning: A Laboratory Manual*, 3rd ed., Cold Spring Harbor Laboratory Press (2001). Various other genetic modifications that functionally delete a gene product are described in the examples below.

Functional deletion can also be accomplished by inhibiting the activity of the gene product, for example, by chemically inhibiting a gene product with a small molecule inhibitor, by expressing a protein that interferes with the activity of the gene product, or by other means.

In certain versions of the invention, the functionally deleted gene product may have less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the activity of the non-functionally deleted gene product.

In certain versions of the invention, a cell with a functionally deleted gene product may have less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the activity of the gene product compared to a cell with the non-functionally deleted gene product.

In certain versions of the invention, the functionally deleted gene product may be expressed at an amount less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the amount of the non-functionally deleted gene product.

In certain versions of the invention, the functionally deleted gene product may result from a genetic modification in which at least 1, at least 2, at least 3, at least 4, at least 5, at least 10, at least 20, at least 30, at least 40, at least 50, or more nonsynonymous substitutions are present in the gene or coding sequence of the gene product.

In certain versions of the invention, the functionally deleted gene product may result from a genetic modification in which at least 1, at least 2, at least 3, at least 4, at least 5, at least 10, at least 20, at least 30, at least 40, at least 50, or more bases are inserted in the gene or coding sequence of the gene product.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of the gene product's gene or coding sequence is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of a promoter driving expression of the gene product is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of an enhancer controlling transcription of the gene product's gene is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of a sequence controlling translation of gene product's mRNA is deleted or mutated.

In certain versions of the invention, the decreased activity or expression of the functionally deleted gene product is determined with respect to the activity or expression of the gene product in its unaltered state as found in nature. In certain versions of the invention, the decreased activity or expression of the functionally deleted gene product is determined with respect to the activity or expression of the gene product in its form in a corresponding microorganism. In certain versions, the genetic modifications giving rise to a functionally deleted gene product are determined with respect to the gene in its unaltered state as found in nature. In certain versions, the genetic modifications giving rise to a functionally deleted gene product are determined with respect to the gene in its form in a corresponding microorganism.

Some versions of the invention include a plurality of microorganisms, wherein greater than about 1%, about 5%, about 10%, about 15%, about 20%, about 25%, about 30%, about 35%, about 40%, about 50%, about 55%, about 60%, about 65%, about 70%, about 75%, about 80%, about 85%, about 90%, about 95%, or more of the plurality of microorganisms comprise a functionally deleted acsA gene product or homolog thereof. In some versions, the plurality of microorganisms is a microbial culture.

Genetic modifications that can be introduced into the acsA gene or homologs thereof to functionally delete the acsA gene product or homologs thereof, such as generating acsA knockouts, are described in the examples below.

The acsA gene is an acetyl-CoA synthetase gene in the exemplary cyanobacterium *Synechococcus* sp. PCC 7002, the coding sequence of which can be found in GenBank under accession number NC_010475.1 and is as follows:

```
                                                    (SEQ ID NO: 1)
atgtccgaac aaaacattga atccatcctc caggagcagc gccttttttc gcctgcacca gactttgctg ccgaggccca gatcaagagc ttagaccagt accaagccct ctacgaccgg gcgaaaaatg accccgaagg cttttggggg gaactcgccg aacaggaatt ggaatggttt gagaaatggg acaaggtgct
```

-continued

```
cgattggcaa ccgcccttcg ccaaatggtt tgtcaacggg aaaattaaca tttcctacaa ttgcctcgac cgtcatctca aaacctggcg caaaaataaa gccgccctca tctgggaagg ggaacccggt gactcccgta ccctcaccta tgcccagcta caccacgagg tctgccagtt tgccaatgcg atgaaaaagt tgggcgtcaa aaaaggcgat cgcgtcggga tttatatgcc aatgatcccg gaagccgtcg ttgccctcct cgcctgtgcc cgcattggtg cgccccatac ggtgatattt ggtggcttta gtgccgaagc cctccgcagt cgcctcgaag acgctgaagc caaactggtg atcaccgccg acggggcctt ccgcaaagat aaagcggtac ccctcaagga tcaagtagat gcggcgatcg ccgatcacca tgcccccagc gttgagaatg ttttggtcgt tcaacgcacc aaagagcctg tccacatgga agccgggcgg gatcactggt ggcatgattt gcaaaaagaa gtctccgctg actgtcccgc cgagccgatg gatgccgaag atatgctctt catcctctat accagcggca ccacgggtaa acccaaggge gttgtccaca ctacgggcgg ttataatctc tacacccata taacgaccaa gtggatcttt gatctcaaag atgatgacgt gtattggtgt ggtgctgatg tgggttggat caccggccac agttacatta cctatggcc tctatctaac ggggcaacgg tcttaatgta tgaaggcgca ccccgtccgt ctaatcccgg ttgctattgg gaaattattc aaaaatatgg tgtcaccatt ttctatacgg cacccacagc gattcgggcc tttatcaaaa tgggtgaagg catcccaat aaatatgaca tgagttccct gcgcctctta ggaaccgtgg gtgaaccgat taacccagaa gcttggatgt ggtaccaccg ggtcattggt ggcgaacgtt gtcccattgt tgatacatgg tggcaaacgg aaaccggtgg tgtgatgatt acgcctttac ccggtgcaac tcccacaaaa cccggctcgg caactcgtcc tttccgggg attgtggcgg atgtcgttga ccttgatgga aattccgttg gtgacaacga aggcggctac ctggtagtga acaaccctg gctgggatg atgcgtactg tttacggcaa tcccgaacgc ttccggtcta cctattggga gcacatcgcc ccgaaagatg gacaatacct ttatttcgca ggtgacgggg cacgccgtga ccaagatggc tatttttgga ttatgggtcg cgtcgatgat gtcttaaatg tttcgggcca tcgcctcggc accatggaag tggaatcggc cctcgtttcc caccctgccg tcgccgaagc agccgtggtt ggaaagccag atccggttaa gggggaagag gtgtttgcct ttgtcaccct tgagggcacc tacagtccga gcgacgatct cgtaacggaa ctcaaggccc atgtggtgaa agaaattggg
```

```
gcgatcgccc gtccgggaga aatccgtttt gccgatgtaa tgcccaaaac ccgttctggg aagatcatgc ggcgtttgtt gcgaaaccta gccgcaggtc aggaaattgt gggcgacacc tccaccctcg aagaccgcag cgtcctcgat caactccggg gctaa
```

The acsA coding sequence in the exemplary organism *Synechococcus* sp. PCC 7002 encodes a protein included in GenBank under accession number YP_001735082.1, having the following amino acid sequence:

(SEQ ID NO: 2)
```
MSEQNIESIL QEQRLFSPAP DFAAEAQIKS LDQYQALYDR

AKNDPEGFWG ELAEQELEWF EKWDKVLDWQ PPFAKWFVNG

KINISYNCLD RHLKTWRKNK AALIWEGEPG DSRTLTYAQL

HHEVCQFANA MKKLGVKKGD RVGIYMPMIP EAVVALLACA

RIGAPHTVIF GGFSAEALRS RLEDAEAKLV ITADGGFRKD

KAVPLKDQVD AAIADHHAPS VENVLVVQRT KEPVHMEAGR

DHWWHDLQKE VSADCPAEPM DAEDMLFILY TSGTTGKPKG

VVHTTGGYNL YTHITTKWIF DLKDDDVYWC GADVGWITGH

SYITYGPLSN GATVLMYEGA PRPSNPGCYW EIIQKYGVTI

FYTAPTAIRA FIKMGEGIPN KYDMSSLRLL GTVGEPINPE

AWMWYHRVIG GERCPIVDTW WQTETGGVMI TPLPGATPTK

PGSATRPFPG IVADVVDLDG NSVGDNEGGY LVVKQPWPGM

MRTVYGNPER FRSTYWEHIA PKDGQYLYFA GDGARRDQDG

YFWIMGRVDD VLNVSGHRLG TMEVESALVS HPAVAEAAVV

GKPDPVKGEE VFAFVTLEGT YSPSDDLVTE LKAHVVKEIG

AIARPGEIRF ADVMPKTRSG KIMRRLLRNL AAGQEIVGDT

STLEDRSVLD QLRG
```

Homologs of acsA include genes or gene products encoded thereby that are homologous to the acsA gene or its product. Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity (e.g., identity) over 50, 100, 150 or more residues (nucleotides or amino acids) is routinely used to establish homology (e.g., over the full length of the two sequences to be compared). Higher levels of sequence similarity (e.g., identity), e.g., 30%, 35% 40%, 45% 50%, 55%, 60%, 65%, 70%, 75%, 80%, 85%, 90%, 95%, or 99% or more, can also be used to establish homology. Accordingly, homologs of the genes or gene products described herein include genes or gene products having at least about 30%, 35%, 40%, 45%, 50%, 55%, 60%, 65%, 70%, 75%, 80%, 85%, 90%, 95%, or 99% identity to the genes or gene products described herein. Methods for determining sequence similarity percentages (e.g., BLASTP and BLASTN using default parameters) are described herein and are generally available. The homologous proteins should demonstrate comparable activities and, if an enzyme, participate in the same or analogous pathways. "Orthologs" are genes in different species that evolved from a common ancestral gene by speciation. Normally, orthologs retain the same or similar function in the course of evolution. As used herein "orthologs" are included in the term "homologs".

For sequence comparison and homology determination, one sequence typically acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence based on the designated program parameters. A typical reference sequence of the invention is a nucleic acid or amino acid sequence corresponding to acsA or other genes or products described herein.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see Current Protocols in Molecular Biology, F. M. Ausubel et al., eds., Current Protocols, a joint venture between Greene Publishing Associates, Inc. and John Wiley & Sons, Inc., (supplemented through 2008)).

One example of an algorithm that is suitable for determining percent sequence identity and sequence similarity for purposes of defining homologs is the BLAST algorithm, which is described in Altschul et al., *J. Mol. Biol.* 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001. The above-described techniques are useful in identifying homologous sequences for use in the methods described herein.

The terms "identical" or "percent identity", in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described above (or other algorithms available to persons of skill) or by visual inspection.

The phrase "substantially identical", in the context of two nucleic acids or polypeptides refers to two or more sequences or subsequences that at least about 60%, about 65%, about 70%, about 75%, about 80%, about 85%, about 90, about 95%, about 98%, or about 99% or more nucleotide or amino acid residue identity, when compared and aligned for maximum correspondence, as measured using a sequence comparison algorithm or by visual inspection. Such "substantially identical" sequences are typically considered to be "homologous", without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, at least about 250 residues, or over the full length of the two sequences to be compared.

Non-limiting examples of gene-product homologs of the acsA gene in various microorganisms include the acetyl-coenzyme A synthetase from *Fischerella* sp. JSC-11 (Genbank Accession No. ZP_08986431.1), the acetyl-coenzyme A from *Moorea producta* 3 L synthetase (Genbank Accession No. ZP_08425677.1), the acetate/CoA from *Cyanothece* sp. PCC 7822 ligase (Genbank Accession No. YP_003886065.1), the acetyl-CoA from *Cyanothece* sp. PCC 7424 synthetase (Genbank Accession No. YP_002378472.1), the unnamed protein product from *Thermosynechococcus elongatus* BP-1 (Genbank Accession No. NP_681677.1), the unnamed protein product from *Anabaena variabilis* ATCC 29413 (Genbank Accession No. YP_321725.1), the acetate-CoA ligase from *Cylindrospermopsis raciborskii* CS-505 (Genbank Accession No. ZP_06308209.1), the acetyl-CoA synthetase from *Nostoc punctiforme* PCC 73102 (Genbank Accession No. YP_001869493.1), the acetate-CoA ligase from *Microcoleus chthonoplastes* PCC 7420 (Genbank Accession No. ZP_05030125.1), the acetyl-coenzyme A synthetase from *Nodularia spumigena* CCY9414 (Genbank Accession No. ZP_01629204.1), the acetyl-CoA synthetase from *Microcystis aeruginosa* NIES-843 (Genbank Accession No.

YP_001660936.1), the acetate/CoA ligase from 'Nostoc azollae' 0708 (Genbank Accession No. YP_003723268.1), the acsA gene from *Microcystis aeruginosa* PCC 7806 (Genbank Accession No. CAO86486.1), the acetyl-coenzyme A synthetase from *Microcoleus vaginatus* FGP-2 (Genbank Accession No. ZP_08490634.1), the Acetate-CoA ligase from *Raphidiopsis brookii* D9 (Genbank Accession No. ZP_06304063.1), the acsA gene product from *Acaryochloris marina* MBIC11017 (Genbank Accession No. YP_001517064.1), the acetyl-CoA synthetase from *Acaryochloris* sp. CCMEE 5410 (Genbank Accession No. ZP_09248274.1), the acetyl-CoA synthetase from *Oscillatoria* sp. PCC 6506 (Genbank Accession No. ZP_07113076.1), the acetyl-CoA synthetase from *Cyanothece* sp. PCC 7425 (Genbank Accession No. YP_002484565.1), the Acetate-CoA ligase from *Lyngbya* sp. PCC 8106 (Genbank Accession No. ZP_01623739.1), the unnamed protein product from *Trichodesmium erythraeum* IMS101 (Genbank Accession No. YP_722064.1), the acetyl-CoA synthetase from *Arthrospira platensis* str. Paraca (Genbank Accession No. ZP_06383883.1), the acetate/CoA ligase from *Arthrospira maxima* CS-328 (Genbank Accession No. ZP_03274675.1), the acetyl-coenzyme A synthetase from *Arthrospira* sp. PCC 8005 (Genbank Accession No. ZP_09782650.1), the acetate/CoA ligase from *Arthrospira maxima* CS-328 (Genbank Accession No. EDZ93724.1), the acetyl-coenzyme A synthetase from *Arthrospira* sp. PCC 8005 (Genbank Accession No. CCE18403.1), the unnamed protein product from *Cyanothece* sp. PCC 8802 (Genbank Accession No. YP_003138301.1), the acetate/CoA ligase from *Cyanothece* sp. PCC 8802 (Genbank Accession No. ACV01466.1), the acetyl-CoA synthetase from *Cyanothece* sp. PCC 8801 (Genbank Accession No. YP_002373634.1), the acetyl-coenzyme A synthetase from *Cyanothece* sp. ATCC 51472 (Genbank Accession No. ZP_08974038.1), the unnamed protein product from *Synechococcus elongatus* PCC 6301 (Genbank Accession No. ZP_08974038.1), the acetyl-CoA synthetase from *Cyanothece* sp. ATCC 51142 (Genbank Accession No. YP_001803432.1), the acetyl-coenzyme A synthetase from *Cyanothece* sp. CCY0110 (Genbank Accession No. ZP_01730332.1), the AMP-dependent synthetase and ligase from *Crocosphaera watsonii* WH 8501 (Genbank Accession No. ZP_00514814.1), the acetate-CoA ligase from *Synechococcus* sp. PCC 7335 (Genbank Accession No. ZP_05036109.1), the acetyl-coenzyme A synthetase from *Synechococcus* sp. WH 8102 (Genbank Accession No. NP_897106.1), the acetate-CoA ligase from *Synechococcus* sp. WH 7805 (Genbank Accession No. ZP_01123920.1), the acetate-CoA ligase from *Synechococcus* sp. WH 8109 (Genbank Accession No. ZP_05788236.1), the acetyl-coenzyme A synthetase from *Prochlorococcus marinus* str. MIT 9313 (Genbank Accession No. NP_894222.1), the acetyl-coenzyme A synthetase from *Prochlorococcus marinus* str. MIT 9303 (Genbank Accession No. YP_001017906.1), the acetyl-CoA synthetase from *Synechococcus* sp. WH 7803 (Genbank Accession No. YP_001224763.1), the acetyl-coenzyme A synthetase from *Synechococcus* sp. RS9917 (Genbank Accession No. ZP_01080065.1), the acetyl-coenzyme A synthetase from *Synechococcus* sp. WH 8016 (Genbank Accession No. ZP_08955323.1), the acetate-CoA ligase from *Synechococcus* sp. CC9311 (Genbank Accession No. YP_730758.1), the acetyl-coenzyme A synthetase from *Prochlorococcus marinus* str. MIT 9211 (Genbank Accession No. YP_001550915.1), the acetate-CoA ligase from *Synechococcus* sp. CC9902 (Genbank Accession No. YP_377326.1), the acetate-CoA ligase from *Synechococcus* sp. BL107 (Genbank Accession No. ZP_01467683.1), the acetyl-coenzyme A synthetase from *Synechococcus* sp. RS9916 (Genbank Accession No. ZP_01471857.1), the acetyl-coenzyme A synthetase from *Synechococcus* sp. CC9605 (Genbank Accession No. YP_381449.1), the acetyl-coenzyme A synthetase from *Synechococcus* sp. CB0205 (Genbank Accession No. ZP_07971118.1), the acetyl-CoA synthetase from *Synechococcus* sp. RCC307 (Genbank Accession No. YP_001227601.1), the acetyl-coenzyme A synthetase from *Synechococcus* sp. CB0101 (Genbank Accession No. ZP_07973216.1), the acetate-CoA ligase from *Cyanobium* sp. PCC 7001 (Genbank Accession No. ZP_05043915.1), the acetate-CoA ligase from *Synechococcus* sp. WH 5701 (Genbank Accession No. ZP_01085120.1), the acs gene product from *Prochlorococcus marinus* subsp. marinus str. CCMP1375 (Genbank Accession No. NP_875433.1), the acetyl-coenzyme A synthetase from *Prochlorococcus marinus* str. NATL2A (Genbank Accession No. YP_291252.1), the acetyl-coenzyme A synthetase from *Gloeobacter violaceus* PCC 7421 (Genbank Accession No. NP_923105.1), the acetyl-coenzyme A synthetase from *cyanobacterium* UCYN-A (Genbank Accession No. YP_003421821.1), the acetyl-coenzyme A synthetase from *Prochlorococcus marinus* str. NATL1A (Genbank Accession No. YP_001014503.1), the acetyl-coenzyme A synthetase from *Singulisphaera acidiphila* DSM 18658 (Genbank Accession No. ZP_09573232.1), the acetyl-coenzyme A synthetase from *Prochlorococcus marinus* subsp. pastoris str. CCMP1986 (Genbank Accession No. NP_892737.1), the acetyl-coenzyme A synthetase from *Prochlorococcus marinus* str. MIT 9312 (Genbank Accession No. YP_397116.1), the acetate/CoA ligase from *Meiothermus ruber* DSM 1279 (Genbank Accession No. YP_003507084.1), the acetyl-coenzyme A synthetase from *Prochlorococcus marinus* str. MIT 9215 (Genbank Accession No. YP_001483902.1), the acs gene product from *Prochlorococcus marinus* str. AS9601 (Genbank Accession No. YP_001009068.1), the acetyl-coenzyme A synthetase from *Prochlorococcus marinus* str. MIT 9515 (Genbank Accession No. YP_001011000.1), the acetate-CoA ligase from *Prochlorococcus marinus* str. MIT 9202 (Genbank Accession No. ZP_05137406.1), the acetyl-coenzyme A synthetase from *Marinithermus hydrothermalis* DSM 14884 (Genbank Accession No. YP_004368660.1), the acetyl-coenzyme A synthetase from *Prochlorococcus marinus* str. MIT 9301 (Genbank Accession No. YP_001090869.1), the unnamed protein product from *Nostoc* sp. PCC 7120 (Genbank Accession No. NP_488297.1), the acetate/CoA ligase from *Truepera radiovictrix* DSM 17093 (Genbank Accession No. YP_003703935.1), the acetate/CoA ligase from *Haliangium ochraceum* DSM 14365 (Genbank Accession No. YP_003269915.1), the acetyl-coenzyme A synthetase from *Gemmata obscuriglobus* UQM 2246 (Genbank Accession No. ZP_02733777.1), the acetyl-coenzyme A synthetase from *Isosphaera pallida* ATCC 43644 (Genbank Accession No. YP_004179760.1), the acetyl-CoA synthetase from *Chloroherpeton thalassium* ATCC 35110 (Genbank Accession No. YP_001995147.1), the acetate-CoA ligase from *Planctomyces maris* DSM 8797 (Genbank Accession No. ZP_01856978.1), the acetyl-CoA synthetase from *Thermus thermophilus* HB8 (Genbank Accession No. YP_144514.1), the acetate/CoA ligase from *Planctomyces limnophilus* DSM 3776 (Genbank Accession No. YP_003632128.1), the acetyl-CoA synthetase from *Thermus thermophilus* HB27 (Genbank Accession No. YP_004855.1), the acetyl-coenzyme a synthetase from *Oceanithermus profundus* DSM 14977 (Genbank Accession No. YP_004057553.1), the acetyl-coenzyme A synthetase from Candidatus Koribacter versatilis Ellin345 (Genbank Accession No. YP_592595.1), the acetate/CoA ligase from Meiothermus silvanus DSM 9946 (Genbank Accession No. YP_003684983.1), the acetate-CoA ligase from Verrucomicrobium spinosum DSM 4136 (Genbank Accession No. ZP_02931268.1), the acetate/CoA ligase from Thermus aquaticus Y51MC23 (Genbank Accession No. ZP_03496427.1), the acetyl-coenzyme A synthetase from Symbiobacterium thermophilum IAM 14863 (Genbank Accession No. YP_074710.1), the acetate/CoA ligase from bacterium Ellin 514 (Genbank Accession No. ZP_03630513.1), the acetyl-CoA synthetase from uncultured candidate division OP1 bacterium (Genbank Accession No. BAL56248.1), the acetyl-coenzyme A synthetase from Blastopirellula marina DSM 3645 (Genbank Accession No. ZP_01092728.1), the acs2 gene product from Thermus scotoductus SA-01 (Genbank Accession No. YP_004201921.1), the acetyl-coenzyme A synthetase from Archaeoglobus veneficus SNP6 (Genbank Accession No. YP_004341076.1), the Acetyl-coenzyme A synthetase from Desulfitobacterium dehalogenans ATCC 51507 (Genbank Accession No. ZP_09634500.1), the unnamed protein product from Candidatus Chloracidobacterium thermophilum B (Genbank Accession No. YP_004864177.1), the acetate-CoA ligase from Acidobacterium capsulatum ATCC 51196 (Genbank Accession No. YP_002755829.1), the acetate/CoA ligase from Pirellula staleyi DSM 6068 (Genbank Accession No. YP_003369860.1), the acetyl-CoA synthetase from Chlorobium chlorochromatii CaD3 (Genbank Accession No. YP_379980.1), the acetate-CoA ligase from Myxococcus xanthus DK 1622 (Genbank Accession No. YP_630789.1), the acetate-CoA ligase from Myxococcus fulvus HW-1 (Genbank Accession No. YP_004667083.1), the unnamed protein product from Candidatus Solibacter usitatus Ellin 6076 (Genbank Accession No. YP_829106.1), the acetyl-coenzyme A synthetase from Planctomyces brasiliensis DSM 5305 (Genbank Accession No. YP_004268501.1), the acetyl-CoA synthetase from Escherichia coli UMN026 (Genbank Accession No. YP_002415210.1), the acetyl-CoA synthetase from Escherichia coli FVEC1412 (Genbank Accession No. ZP_06646805.1), the acetyl-coenzyme A synthetase from Escherichia coli FVEC1302 (Genbank Accession No. ZP_06988121.1), the acetate-CoA ligase from Escherichia coli MS 198-1 (Genbank Accession No. ZP_07115900.1), the acetyl-CoA synthetase from Escherichia coli UMN026 (Genbank Accession No. CAR15720.1), the Acs2p from Saccharomyces cerevisiae S288c (Genbank Accession No. NP_013254.1), the acetyl CoA synthetase from Saccharomyces cerevisiae YJM789 (Genbank Accession No. EDN59693.1), the K7_Acs2p from Saccharomyces cerevisiae Kyokai no. 7 (Genbank Accession No. GAA25035.1), the acetyl CoA synthetase from Saccharomyces cerevisiae RM11-1a (Genbank Accession No. EDV09449.1), the bifunctional acetyl-CoA synthetase and propionyl-CoA synthetase from Escherichia coli str. K12 substr. W3110 (GenBank Accession No. BAE78071.1), and the acetyl-coenzyme A synthetase from Pseudomonas fulva 12-X (GenBank Accession No. YP_004473024.1), among others. The genes encoding these gene products can be found in GenBank (http://www.ncbi.nlm.nih.gov/genbank/).

Homologs of acsA and AcsA discussed in the examples include the acetyl-CoA synthetase from Synechocystis sp. PCC 6803 (sll0542; Genbank Accession No. NP_442428.1; SEQ ID NOS:3 and 4), and the unnamed protein product from Synechococcus sp. PCC 7942 (SYNPCC7942_1342; Genbank Accession No. YP_400369.1; SEQ ID NOS:5 and 6)

The organic acid-tolerant microorganism of the present invention may include any microorganism that harbors an acsA gene or homolog thereof or expresses an acsA gene product or homolog thereof that is capable of being functionally deleted to render the microorganism more tolerant of organic acids. The microorganism may be eukaryotic, such as yeast, or prokaryotic, such as bacteria or archaea. Among bacteria, gram-positive, gram-negative, and ungrouped bacteria are suitable. Phototrophs, lithotrophs, and organotrophs are also suitable. In preferred versions of the invention, the microorganism is a phototroph, such as a cyanobacterium. Preferred cyanobacteria include those selected from the group consisting of Synechococcus sp., Prochlorococcus sp., Synechocystis sp., and Nostoc sp., with particularly suitable examples of Synechococcus sp. including Synechococcus sp. PCC 7942, Synechocystis sp. PCC 6803, and Synechococcus sp. PCC 7002. A benefit of phototrophs is that they require only $CO_2$ as a carbon source and are not dependent on food-based commodities or other types of biomass for which there is a growing high demand.

Functional deletion of the acsA gene product or homolog thereof in the microorganism results in increased tolerance of the microorganism to organic acids compared to a corresponding microorganism. As used herein, "corresponding microorganism" refers to a microorganism of the same species having the same or substantially same genetic and proteomic composition as a microorganism of the invention, with the exception of genetic and proteomic differences resulting from the modifications described herein for the microorganisms of the invention. Such tolerance is with respect to any organic acid present within the organism or its growth medium, particularly those that may be present in high abundance. Non-limiting examples of organic acids to which the microorganisms of the present invention have increased tolerance include acetic acid, acrylic acid, aspartic acid, benzoic acid, butyric acid, citric acid, formic acid, fumaric acid, furan dicarboxylic acid (2,5-furandicarboxylic acid), glucaric acid, glutamic acid, heptanoic acid, hexanoic acid, 3-hydroxypropionic acid (3HP), isophthalic acid, itaconic acid, lactic acid, levoascorbic acid, levulinic acid, malic acid, octanoic acid, oxalic acid, pentanoic acid, phosphoric acid, propionic acid, pyruvic acid, succinic acid (1,4 succinic acid), and terephthalic acid, among others. The examples show various aspects of increased tolerance to exemplary organic acids 3-hydroxypropionic acid (3HP), acrylic acid, and propionic acid.

One aspect of the increased tolerance to organic acids is an increase in the minimal inhibitory concentration (MIC) of a particular organic acid compared to a corresponding microorganism. MIC is the lowest concentration of an agent that will inhibit growth of a microorganism. An MIC can be determined by titrating the agent in the growth medium of the microorganism. The lowest concentration of the agent in which the microorganism is no longer able to grow is the MIC. Methods of culturing microorganisms and of detecting their growth are well known in the art and are not discussed in detail herein. A relative increase in MIC indicates a higher tolerance to an agent and indicates that the microorganism can grow in the presence of a higher concentration of the agent. Conversely, a relative decrease in MIC indicates a lower tolerance to an agent and indicates that the microorganism can grow only in the presence of a lower concentration of the agent.

Functional deletion of the acsA gene product or homolog thereof in the microorganism confers an MIC of at least about 10 µM, 25 µM, 50 µM, 75 µM, 100 µM, 250 µM, 500 µM, 1 mM, 25 mM, 50 mM, 70 mM, 100 mM, 125 mM, or 150 mM to acrylic acid; an MIC of at least about 10 mM, 15 mM, 20 mM, 25 mM, 50 mM, 75 mM, 100 mM, 125 mM, 150 mM, 175 mM, 200 mM, 225 mM, 250 mM, 260 mM, 300 mM, 350 mM, or more to 3HP; and/or an MIC of at least about 250 µM, 500 µM, 1 mM, 50 mM, 100 mM, 200 mM, 300 mM, 350 mM, 400 mM, 450 mM, 500 mM, or more to propionic acid. Such MICs occur in at least *Synechococcus* sp. cyanobacteria, such as *Synechococcus* sp. PCC 7002 and *Synechococcus* sp. PCC 7942, when assayed at a pH of about 8. Such MICs also occur in *Synechocystis* sp., such as *Synechocystis* sp. PCC 6803, when assayed at a pH of about 8. Such MICs also occur in any other microorganism described herein, such as *Prochlorococcus* sp., *Nostoc* sp., or others.

Another aspect of increased tolerance is increased growth rate in the presence of a certain concentration of an organic acid or an equal growth rate in the presence of an increased concentration of an organic acid compared to a corresponding microorganism.

In various aspects of the invention, functional deletion of the acsA gene product or homolog thereof in the microorganism confers at least about a 1.5-fold, a 5-fold, a 10-fold, a 15-fold, a 25-fold, a 50-fold, a 75-fold, a 100-fold, a 500-fold, a 750-fold, a 1,000-fold, 1,250-fold, a 1,500-fold, a 1,750-fold, a 2,000-fold, a 2,250-fold, a 2,500-fold, a 2,750-fold, a 3,000-fold, a 3,250-fold, or a 3,500-fold increase in tolerance against an organic acid. The organic acid to which functional deletion of the acsA gene product confers such MICs may include acrylic acid, 3HP, or propionic acid, among others. In some versions of the invention, for example, functional deletion of the acsA gene product in *Synechococcus* sp. PCC 7002 confers at least about a 2,800-fold increase in MIC for acrylic acid, at least about a 26-fold increase in MIC for 3HP, and at least about a 100-fold increase in MIC for propionic acid at pH of about 8 (see examples below).

The increased tolerance to organic acids conferred by functional deletion of the acsA gene product or homolog thereof renders the microorganism particularly suited for producing high amounts of organic acids, many of which have industrial utility. Accordingly, the microorganism in some versions of the invention is capable of producing an organic acid that can be isolated for industrial purposes. The microorganism may be able to naturally make the organic acid, may be genetically modified to make the organic acid, or may be genetically modified to make increased amounts of the organic acid that it already makes. Non-limiting examples of organic acids that the microorganisms of the present invention can produce include acetic acid, aspartic acid, benzoic acid, citric acid, formic acid, fumaric acid, furan dicarboxylic acid (2,5-furandicarboxylic acid), glucaric acid, glutamic acid, 3-hydroxypropionic acid (3HP), isophthalic acid, itaconic acid, lactic acid, levoascorbic acid, levulinic acid, malic acid, oxalic acid, phosphoric acid, propionic acid, pyruvic acid, succinic acid (1,4 succinic acid), and terephthalic acid, among others. In preferred versions of the invention, the microorganism is capable of making at least 3HP.

In preferred versions of the invention, the microorganism is genetically modified to enhance production of at least 3HP. This can be performed by increasing expression of a gene for any one or more of the enzymes catalyzing the various steps in a 3HP-production pathway. Non-limiting examples of suitable enzymes include pyruvate kinase, pyruvate dehydrogenase, acetyl-CoA carboxylase, malonyl-CoA reductase, phosphoenolpyruvate carboxylase, aspartate aminotransferase, aspartate decarboxylase, and β-alanine/α-ketoglutarate aminotransferase. See FIG. 7. See also U.S. Pat. No. 8,048,624 to Lynch, U.S. Pub. 2011/0125118 to Lynch, U.S. Pub. 2010/0210017 to Gill et al., and Warnecke et al. *Metabolic Engineering* (2010) 12:241-250 for additional enzymes. Increasing expression can be performed using any of methods currently known in the art or discovered in the future. Examples include genetic modification of the microorganism as well as culturing the microorganism in the presence of factors that increase expression of the gene. Suitable methods for genetic modification include but are not limited to placing the gene under the control of a more active promoter, increasing the copy number of the gene, and/or introducing a translational enhancer on the gene (see, e.g., Olins et al. *Journal of Biological Chemistry,* 1989, 264(29):16973-16976). Increasing the copy number of the gene can be performed by introducing additional copies of the gene to the microorganism, i.e., by incorporating one or more exogenous copies of the native gene or a heterologous homolog thereof into the microbial genome, by introducing such copies to the microorganism on a plasmid or other vector, or by other means. "Exogenous" used in reference to a genetic element means the genetic element is introduced to a microorganism by genetic modification. "Heterologous" used in reference to a genetic element means that the genetic element is derived from a different species. A promoter that controls a particular gene is herein described as being "operationally connected" to the gene.

Accordingly, some microorganisms of the invention include at least one recombinant nucleic acid configured to overexpress a 3HP pathway enzyme. "Recombinant" as used herein with reference to a nucleic acid molecule or polypeptide is one that has a sequence that is not naturally occurring, has a sequence that is made by an artificial combination of two otherwise separated segments of sequence, or both. This artificial combination can be achieved, for example, by chemical synthesis or by the artificial manipulation of isolated segments of nucleic acid molecules or polypeptides, such as genetic engineering techniques. "Recombinant" is also used to describe nucleic acid molecules that have been artificially modified but contain the same regulatory sequences and coding regions that are found in the organism from which the nucleic acid was isolated. A recombinant cell or microorganism is one that contains a recombinant nucleic acid molecule or polypeptide. "Overexpress" as used herein means that a particular gene product is produced at a higher level in one cell, such as a recombinant cell, than in a corresponding cell. For example, a microorganism that includes a recombinant nucleic acid configured to overexpress an enzyme produces the enzyme at a greater amount than a microorganism that does not include the recombinant nucleic acid.

In a preferred version of the invention, the microorganism is manipulated to express or increase expression of malonyl-CoA reductase. In some versions, the microorganism is modified to harbor a nucleic acid derived from *Chloroflexus aurantiacus* that encodes a malonyl-CoA reductase gene or a homolog thereof. The *Chloroflexus aurantiacus* malonyl-CoA reductase gene is included in GenBank under accession number AY530019 and has the following nucleotide sequence:

```
                                             SEQ ID NO: 7)
aacatcatgg tatactatac ctatcgataa ttcttcaact aattgcataa cagaacagcg atggcgacgg gggagtccat gagcggaaca ggacgactgg caggaaagat tgcgttaatt accggtggcg ccggcaatat cggcagtgaa ttgacacgtc gctttctcgc agagggagcg acggtcatta ttagtggacg
```

-continued

```
gaatcgggcg aagttgaccg cactggccga acggatgcag
gcagaggcag gagtgccggc aaagcgcatc gatctcgaag
tcatggatgg gagtgatccg gtcgcggtac gtgccggtat
cgaagcgatt gtggcccgtc acggccagat cgacattctg
gtcaacaatg caggaagtgc cggtgcccag cgtcgtctgg
ccgagattcc actcactgaa gctgaattag ccctggcgc
cgaagagacg cttcatgcca gcatcgccaa tttacttggt
atgggatggc atctgatgcg tattgcggca cctcatatgc
cggtaggaag tgcggtcatc aatgtctcga ccatcttttc
acgggctgag tactacgggc ggattccgta tgtcacccct
aaagctgctc ttaatgctct atctcaactt gctgcgcgtg
agttaggtgc acgtggcatc cgcgttaata cgatctttcc
cggcccgatt gaaagtgatc gcatccgtac agtgttccag
cgtatggatc agctcaaggg gcggcccgaa ggcgacacag
cgcaccattt tttgaacacc atgcgattgt gtcgtgccaa
cgaccaggc gcgcttgaac gtcggttccc ctccgtcggt
gatgtggcag acgccgctgt ctttctggcc agtgccgaat
ccgccgctct ctccggtgag acgattgagg ttacgcacgg
aatggagttg ccggcctgca gtgagaccag cctgctggcc
cgtactgatc tgcgcacgat tgatgccagt ggccgcacga
cgctcatctg cgccggcgac cagattgaag aggtgatggc
gctcaccggt atgttgcgta cctgtgggag tgaagtgatc
atcggcttcc gttcggctgc ggcgctggcc cagttcgagc
aggcagtcaa tgagagtcgg cggctggccg gcgcagactt
tacgcctccc attgccttgc cactcgatcc acgcgatccg
gcaacaattg acgctgtctt cgattgggg gccggcgaga
ataccggcgg gattcatgca gcggtgattc tgcctgctac
cagtcacgaa ccggcaccgt gcgtgattga ggttgatgat
gagcgggtgc tgaatttct ggccgatgaa atcaccggga
caattgtgat tgccagtcgc ctggcccgtt actggcagtc
gcaacggctt accccggcg cacgtgcgcg tgggccgcgt
gtcattttc tctcgaacgg tgccgatcaa aatgggaatg
tttacggacg cattcaaagt gccgctatcg gtcagctcat
tcgtgtgtgg cgtcacgagg ctgaacttga ctatcagcgt
gccagcgccg ccggtgatca tgtgctgccg ccggtatggg
ccaatcagat tgtgcgcttc gctaaccgca gccttgaagg
gttagaattt gcctgtgcct ggacagctca attgctccat
agtcaacgcc atatcaatga gattaccctc aacatccctg
ccaacattag cgccaccacc ggcgcacgca gtgcatcggt
cggatgggcg gaaagcctga tcgggttgca tttggggaaa
```

-continued

```
gttgccttga ttaccggtg cagcgccggt attggtgggc
agatcgggcg cctcctggct ttgagtggcg cgcgcgtgat
gctggcagcc cgtgatcggc ataagctcga acagatgcag
gcgatgatcc aatctgagct ggctgaggtg gggtataccg
atgtcgaaga tcgcgtccac attgcaccgg gctgcgatgt
gagtagcgaa gcgcagcttg cggatcttgt tgaacgtacc
ctgtcagctt ttggcaccgt cgattatctg atcaacaacg
ccgggatcgc cggtgtcgaa gagatggtta tcgatatgcc
agttgaggga tggcgccata ccctcttcgc caatctgatc
agcaactact cgttgatgcg caaactggcg ccgttgatga
aaaaacaggg tagcggttac atccttaacg tctcatcata
cttttggcggt gaaaaagatg cggccattcc ctaccccaac
cgtgccgatt acgccgtctc gaaggctggt cagcgggcaa
tggccgaagt cttttgcgcgc ttccttggcc cggagataca
gatcaatgcc attgcgccgg gtccggtcga aggtgatcgc
ttgcgcggta ccggtgaacg tcccggcctc tttgcccgtc
gggcgcggct gattttggag aacaagcggc tgaatgagct
tcacgctgct cttatcgcgg ctgcgcgcac cgatgagcga
tctatgcacg aactggttga actgctctta cccaatgatg
tggccgcact agagcagaat cccgcagcac ctaccgcgtt
gcgtgaactg gcacgacgtt ttcgcagcga aggcgatccg
gcggcatcat caagcagtgc gctgctgaac cgttcaattg
ccgctaaatt gctggctcgt ttgcataatg gtggctatgt
gttgcctgcc gacatctttg caaacctgcc aaacccgccc
gatcccttct tcacccgagc ccagattgat cgcgaggctc
gcaaggttcg tgacggcatc atggggatgc tctacctgca
acggatgccg actgagtttg atgtcgcaat ggccaccgtc
tattaccttg ccgaccgcaa tgtcagtggt gagacattcc
acccatcagg tggtttgcgt tacgaacgca cccctaccgg
tggcgaactc ttcggcttgc cctcaccgga acggctggcg
gagctggtcg gaagcacggc tatctgata ggtgaacatc
tgactgaaca ccttaacctg cttgcccgtg cgtacctcga
acgttacggg gcacgtcagg tagtgatgat tgttgagaca
gaaaccgggg cagagacaat gcgtcgcttg ctccacgatc
acgtcgaggc tggtcggctg atgactattg tggccggtga
tcagatcgaa gccgctatcg accaggctat cactcgctac
ggtcgcccag ggccggtcgt ctgtaccccc ttccggccac
tgccgacggt accactggtc gggcgtaaag acagtgactg
gagcacagtg ttgagtgagg ctgaatttgc cgagttgtgc
gaacaccagc tcacccacca tttccgggta gcgcgcaaga
ttgccctgag tgatggtgcc agtctcgcgc tggtcactcc
```

```
cgaaactacg gctacctcaa ctaccgagca atttgctctg gctaacttca tcaaaacgac ccttcacgct tttacggcta cgattggtgt cgagagcgaa agaactgctc agcgcattct gatcaatcaa gtcgatctga cccggcgtgc gcgtgccgaa gagccgcgtg atccgcacga gcgtcaacaa gaactggaac gttttatcga ggcagtcttg ctggtcactg caccactccc gcctgaagcc gatacccgtt acgccgggcg gattcatcgc ggacgggcga ttaccgtgta aattctacgc cacaggaacc actaccaaac cagcatagta agagaacgat agagacgttg caatgcgacg tctctatcat atttccggcc cccctagac aaaccccac gtcttcgtgt agactagaaa caggaggctg tatgcacgtc caacaaga
```

The *Chloroflexus aurantiacus* malonyl-CoA reductase gene product is included in GenBank under accession number AAS20429 and has the following amino acid sequence:

```
                                              (SEQ ID NO: 8)
MSGTGRLAGK IALITGGAGN IGSELTRRFL AEGATVIISG

RNRAKLTALA ERMQAEAGVP AKRIDLEVMD GSDPVAVRAG

IEAIVARHGQ IDILVNNAGS AGAQRRLAEI PLTEAELGPG

AEETLHASIA NLLGMGWHLM RIAAPHMPVG SAVINVSTIF

SRAEYYGRIP YVTPKAALNA LSQLAARELG ARGIRVNTIF

PGPIESDRIR TVFQRMDQLK GRPEGDTAHH FLNTMRLCRA

NDQGALERRF PSVGDVADAA VFLASAESAA LSGETIEVTH

GMELPACSET SLLARTDLRT IDASGRTTLI CAGDQIEEVM

ALTGMLRTCG SEVIIGFRSA AALAQFEQAV NESRRLAGAD

FTPPIALPLD PRDPATIDAV FDWGAGENTG GIHAAVILPA

TSHEPAPCVI EVDDERVLNF LADEITGTIV IASRLARYWQ

SQRLTPGARA RGPRVIFLSN GADQNGNVYG RIQSAAIGQL

IRVWRHEAEL DYQRASAAGD HVLPPVWANQ IVRFANRSLE

GLEFACAWTA QLLHSQRHIN EITLNIPANI SATTGARSAS

VGWAESLIGL HLGKVALITG GSAGIGGQIG RLLALSGARV

MLAARDRHKL EQMQAMIQSE LAEVGYTDVE DRVHIAPGCD

VSSEAQLADL VERTLSAFGT VDYLINNAGI AGVEEMVIDM

PVEGWRHTLF ANLISNYSLM RKLAPLMKKQ GSGYILNVSS

YFGGEKDAAI PYPNRADYAV SKAGQRAMAE VFARFLGPEI

QINAIAPGPV EGDRLRGTGE RPGLFARRAR LILENKRLNE

LHAALIAAAR TDERSMHELV ELLLPNDVAA LEQNPAAPTA

LRELARRFRS EGDPAASSSS ALLNRSIAAK LLARLHNGGY

VLPADIFANL PNPPDPFFTR AQIDREARKV RDGIMGMLYL

QRMPTEFDVA MATVYYLADR NVSGETFHPS GGLRYERTPT

GGELFGLPSP ERLAELVGST VYLIGEHLTE HLNLLARAYL

ERYGARQVVM IVETETGAET MRRLLHDHVE AGRLMTIVAG

DQIEAAIDQA ITRYGRPGPV VCTPFRPLPT VPLVGRKDSD

WSTVLSEAEF AELCEHQLTH HFRVARKIAL SDGASLALVT

PETTATSTTE QFALANFIKT TLHAFTATIG VESERTAQRI

LINQVDLTRR ARAEEPRDPH ERQQELERFI EAVLLVTAPL

PPEADTRYAG RIHRGRAITV
```

Exemplary homologs of the *Chloroflexus aurantiacus* malonyl-CoA reductase gene product include but are not limited to the short-chain dehydrogenase/reductase SDR from *Chloroflexus aggregans* DSM 9485 (Genbank Accession No. YP_002462600.1), the short-chain dehydrogenase/reductase SDR from *Oscillochloris trichoides* DG6 (Genbank Accession No. ZP_07684596.1), the short-chain dehydrogenase/reductase SDR from *Roseiflexus castenholzii* DSM 13941 (Genbank Accession No. YP_001433009.1), the short-chain dehydrogenase/reductase SDR from *Roseiflexus* sp. RS-1 (Genbank Accession No. YP_001277512.1), among others. The genes encoding these gene products can be found in GenBank.

In some versions of the invention, the microorganism is manipulated to express or increase expression of acetyl-CoA carboxylase, either alone, with malonyl-CoA reductase, or with other enzymes. This can be performed by introducing exogenous acetyl-CoA carboxylase subunit genes into the microorganism, by introducing highly expressed promoters in front of the endogenous acetyl-CoA carboxylase subunit genes, by increasing translational efficiency, or by other means. In bacteria, acetyl-CoA carboxylase is a multisubunit enzyme that is encoded by four genes, accA, accB, accC, and accD. Exemplary acetyl-coA carboxylase subunit genes for use in the present invention can be those found in *Synechococcus* sp. PCC 7002 or homologs thereof. The complete genome of *Synechococcus* sp. PCC 7002 can be found in GenBank under Accession No. NC_010475. The gene for accA can be found at positions 2536162-2537139 of NC_010475, the gene product of which has a sequence represented by GenBank Accession No. YP_001735676.1. The gene for accB can be found at positions 60707-61204 of NC_010475, the gene product of which has a sequence represented by GenBank Accession No. YP_001733325.1. The gene for accC can be found at positions 2210473-2211819 of NC_010475, the gene product of which has a sequence represented by GenBank Accession No. YP_001735364.1". The gene for accD can be found at positions 64484-65443 of NC_010475, the gene product of which has a sequence represented by GenBank Accession No. YP_001733331.1. Suitable promoters for increasing expression of these genes are known in the art. In some versions of the invention, an artificial operon comprising the accD, accA, accB, and accC subunits from *E. coli* can be introduced into the microorganism for expression or overexpression of acetyl-CoA carboxylase. See, e.g., US 2011/0165637 to Pfleger et al., which is incorporated herein by reference.

Other genetic modifications of the microorganism of the present invention include any of those described in U.S. Pat. No. 8,048,624 to Lynch, U.S. Pub. 2011/0125118 to Lynch, and U.S. Pub. 2010/0210017 to Gill et al., all of which are attached hereto. See also Warnecke et al. *Metabolic Engineering* (2010) 12:241-250. The genetic modifications in these references may be to enhance organic acid tolerance and/or increase organic acid production. The microorganism of the present invention may also be modified with homologs of any of the genes, constructs, or other nucleic acids discussed in the above references. Non-limiting examples of the genes that may be manipulated or introduced include tyrA, aroA, aroB, aroC, aroD, aroE, aroF, aroG, aroH, aroK, aroL, aspC, entA, entB, entC, entD, entE, entF, folA, folB, folC, folD, folE, folK, folP, menA, menB, menC, menD, menE, menF, pabA, pabB, pabC, pheA, purN, trpA, trpB, trpC, trpD, trpE, tyrB, ubiA, ubiB, ubiG, ubiD, ubiE, ubiF, ubiG, ubiH, ubiX, and ydiB, or homologs thereof. A non-limiting example of a pathway that may be manipulated includes the chorismate superpathway. These genes and pathways are primarily but not exclusively related to the production and tolerance of 3HP.

Exogenous, heterologous nucleic acids encoding enzymes to be expressed in the microorganism are preferably codon-optimized for the particular microorganism in which they are introduced. Codon optimization can be performed for any nucleic acid by a number of programs, including "GENEGPS"-brand expression optimization algorithm by DNA 2.0 (Menlo Park, Calif.), "GENEOPTIMIZER"-brand gene optimization software by Life Technologies (Grand Island, N.Y.), and "OPTIMUMGENE"-brand gene design system by GenScript (Piscataway, N.J.). Other codon optimization programs or services are well known and commercially available.

In addition to the microorganism itself, other aspects of the present invention include methods of producing organic acids with the microorganisms of the present invention. The methods involve culturing the microorganism in conditions suitable for growth of the microorganism. The microorganism either directly produces the organic acid or acids of interest or produces organic-acid precursors from which the organic acid or acids of interest are spontaneously converted. Such conditions include providing suitable carbon sources for the particular microorganism along with suitable micronutrients. For eukaryotic microorganisms and heterotrophic bacteria, suitable carbon sources include various carbohydrates. Such carbohydrates may include biomass or other suitable carbon sources known in the art. For phototrophic bacteria, suitable carbon sources include $CO_2$, which is provided together with light energy.

The microorganism of the present invention is capable of being cultured in high concentrations of the organic acid or acids that the organism is configured to produce. This enables increased production of the organic acid or acids of interest. The microorganism can be cultured in the presence of an organic acid in an amount up to the MIC for that organic acid. Various MICs for exemplary organic acids are described herein. Accordingly, the microorganisms of the invention (i.e., *Synechococcus* sp., *Prochlorococcus* sp., etc.) can be cultured in the presence of at least about 10 µM, 25 µM, 50 µM, 75 µM, 100 µM, 250 µM, 500 µM, 750 µM, 1 mM, 25 mM, 50 mM, 70 mM, 75 mM, 100 mM, 125 mM, or 150 mM acrylic acid; at least about 10 mM, 25 mM, 50 mM, 75 mM, 100 mM, 150 mM, 200 mM, 250 mM, 260 mM, 300 mM, or 350 mM 3HP; and/or at least about 250 µM, 500 µM, 750 µM, 1 mM, 25 mM, 50 mM, 75 mM, 100 mM, 150 mM, 200 mM, 250 mM, 300 mM, 350 mM, 400 mM, 450 mM, or 500 mM propionic acid. Such culturing preferably occurs at a pH of about 8.

Some versions of the invention include using acsA or a homolog thereof as a counter selection marker. The acsA or homolog thereof provides sensitivity to the organic acids acrylic acid, 3HP, and propionic acid. By replacing the native copy of acsA or homolog thereof with a gene of interest through double homologous recombination, one can select for cells which have gone through the recombination event by plating on acrylic acid or another organic acid as described herein. Acrylic acid is preferred because it has the lowest MIC value and requires the lowest concentration for selection. Through this method, one can introduce a gene or operon of interest onto a chromosome without the need for antibiotics. Additionally, one can plate on a higher organic acid concentration, i.e., one closer to the MIC value of the acsA mutant strain, to cure the strain of interest of any copies of the wild type chromosome. This is of particular interest because it can be difficult to create a homozygous strain using antibiotics as the selection agent.

One version comprises using acsA or homolog thereof as a counter selection marker for introducing DNA fragments of interest into the acsA or homolog locus. An exemplary version is shown in FIG. 1A. A host 10 is transformed with either linear DNA fragments or plasmid DNA comprising a sequence of interest 12 flanked by an upstream homologous sequence 14 and a downstream homologous sequence 16. For introducing the sequence of interest 12 into the acsA locus, the upstream homologous sequence 14 is preferably homologous to a region 15 5' of the acsA or homolog 19 on the host chromosome 18, and the downstream homologous sequence 16 is preferably homologous to a region 17 3' of the ascsA or homolog 19 on the host chromosome 18. The homologous sequences 14,16 are preferably at least about 25-base pairs (bp), about 50-bp, about 100-bp, about 200-bp, about 300-bp, about 400-bp, or about 500-bp long. The transformed culture is then plated in a concentration of an organic acid sufficient to select for transformed cells. In preferred versions, the transformed culture is plated in a sub-MIC concentration of an organic acid, such as a concentration greater than 0% the MIC but less than about 20% the MIC, about 40% the MIC, about 50% the MIC, about 60% the MIC, or about 70% the MIC. After colonies appear, the colonies are then plated on a higher concentration of the organic acid to ensure homozygosity.

Figure 1B:
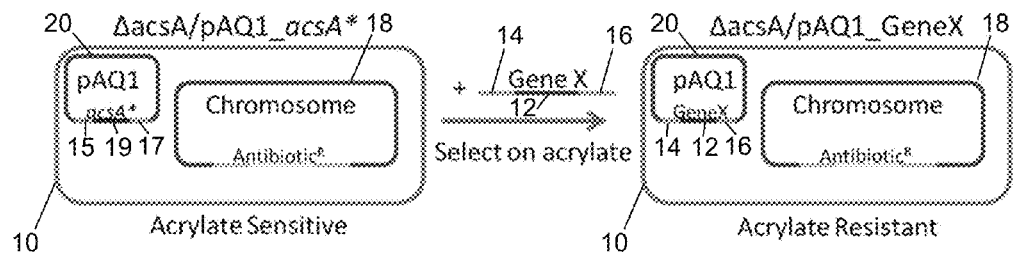
FIG. 1B depicts a schema for using acsA or a homolog thereof as a selection marker for introducing a DNA fragment of interest into a locus other than the acsA or homolog chromosomal locus.

Another version comprises using the acsA gene or homolog thereof as a counter selection marker to introduce DNA fragments of interest into loci other than an acsA or homolog locus without leaving an antibiotic resistance marker. An exemplary version is shown in FIG. 1B. The version shown in FIG. 1B is similar to that shown in FIG. 1A except that the acsA or homolog thereof 19 is not at the normal chromosomal locus. In the specific case of FIG. 1B, a homolog of acsA, acsA*, is included on a non-chromosomal plasmid 20. The acsA or homolog thereof 19 can also be at a locus on the chromosome 18 other than the native acsA or homolog locus. The upstream homologous sequence 14 in FIG. 1B is homologous to a region 15 5' of the acsA or homolog 19 on the non-chromosomal plasmid 20, and the downstream homologous sequence 16 is homologous to a region 17 3' of the acsA or homolog 19 on the on the non-chromosomal plasmid 20.

To increase the utility of acsA as a counter selection marker, two point mutations can be made, T144C and G150C. These point mutations maintain the same amino acid sequence but break up a run of base pairs that create a loss of function mutation hot spot. By creating these mutations, the background mutation frequency of this gene is reduced. This mutant version of acsA, acsA*, can be incorporated onto a non-chromosomal plasmid, such as the endogenous plasmid pAQ1 of a ΔacsA strain of PCC 7002. This base strain allows for incorporating a gene or operon of interest onto the pAQ1 plasmid without the use of antibiotics and quickly creating a homozygous strain.

The elements and method steps described herein can be used in any combination whether explicitly described or not.

The singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the following claims.

EXAMPLES

Summary of the Examples

One of the potential applications of metabolic engineering is the use of cyanobacteria to photosynthetically produce commodity chemicals traditionally derived from petroleum. In particular, acrylic acid has been identified as a high-value product that could be biologically derived. Unfortunately, a viable metabolic pathway has not previously been identified for its direct production.

As described in further detail below, a mutation resulting in increased tolerance to 3HP was discovered through investigating the metabolism of a sulfur compound, dimethylsulfoniopropionate (DMSP), by *Synechococcus* sp. PCC 7002 (PCC 7002). PCC 7002 was grown in the presence of DMSP to determine if it could be metabolized. This surprisingly resulted in the accumulation of acrylic acid, a by-product of DMSP metabolism, showing that *Synechococcus* sp. can produce acrylic acid. The accumulation of acrylic acid in the growth medium caused a stall in growth of the cyanobacteria, suggesting it had a toxic effect. After an additional incubation period, growth began to resume. It was originally hypothesized that the ability to grow in the presence of acrylic acid was the result of an adaptation to the stress through altered gene regulation. This hypothesis was later invalidated after an experiment was performed involving growing "unadapted" cells on solid medium containing acrylic acid. The number of colonies on the plate relative to a control suggested that a loss of function mutation was occurring that resulted in the ability to grow in the presence of acrylic acid. Additionally, all mutants obtained through growth in the presence of acrylic acid had increased tolerance levels to 3HP. The increase in tolerance caused by the mutation resulted in a strain of cyanobacteria constituting a platform for either 3HP or acrylic acid production.

Steps were taken to identify the site of the mutation. An RNA sequencing experiment was performed to characterize differential gene expression in the presence of either DMSP or acrylic acid. This data set was used to identify genes that had single base pair mutations relative to the wild type strain. Through this analysis, mutations were identified in the gene acsA. In order to determine if acsA was involved in acrylic acid and 3HP toxicity, a strain of PCC 7002 was created that had a deletion of the acsA gene. This strain, PCC 7002 ΔacsA, had increased MIC values compared to wild type PCC 7002. These experiments determined that it is a loss of function of acsA that results in increased tolerance. The gene acsA was annotated as an acetyl-CoA ligase.

In order to demonstrate the utility of the ΔacsA strain, a pathway for producing 3HP was introduced into both the wild type PCC 7002 and ΔacsA strains. Several pathways exist for the production of 3HP from central metabolites. The chosen pathway involves an enzyme from the $CO_2$ fixation pathway of the thermophilic bacterium *Chloroflexus aurantiacus*. In this pathway, malonyl-CoA is converted to 3HP through a two-step reaction catalyzed by the enzyme malonyl-CoA reductase. Results have shown that expression of malonyl-CoA reductase confers the ability to produce 3HP on the order of 50 µM.

The result of these experiments is an engineered strain of PCC 7002 that can produce 3HP and is more tolerant to 3HP than wild type PCC 7002 or other cyanobacterial species. Further work will increase the yield of 3HP. The approach to increasing yield will involve further metabolic engineering and optimizing of culturing conditions. To further engineer this strain, expression of the malonyl-CoA reductase will be optimized and genes related to making malonyl-CoA will be over-expressed. Additionally, the current and further engineered strains will be cultured in a photobioreactor in order to monitor 3HP production under optimal growth conditions, and culture parameters will be adjusted to increase yields. The outcome of this work will be a strain of cyanobacteria with optimized culturing conditions that will result in a competitive yield of 3HP.

Background and Significance of Examples

Engineering Bacteria to Produce Commodity Chemicals

A current focus of metabolic engineering and synthetic biology is the development of new methods for producing commodity chemicals that are traditionally produced from petroleum [1,2]. Demand for methods of bioconversion of renewable resources (biomass or $CO_2$) to these compounds has increased due to price volatility and reliance on foreign production of oil, concerns of increasing atmospheric $CO_2$, and increased consumer demand for "green" and sustainable products. An example of recent commercial success is the production of 1,3-propanediol (a precursor of nylon-like materials) by DuPont via *Escherichia coli* fermentation of corn sugar [3].

Another compound that could be produced from renewable sources is acrylic acid. Acrylic acid, traditionally produced through the oxidation of propene, is used in coatings, finishes, plastics, and superabsorbent polymers [4]. US demand for acrylic acid continues to grow, exceeding $1\times10^9$ kg/year, and is outpacing current production [4]. For this reason, non-petroleum based, sustainable methods for producing acrylic acid would be of value. Unfortunately, a thermodynamically favorable pathway for complete biological production of acrylic acid has not been identified [5]. An alternative route would be biological production of 3-hydroxypropionic acid (3HP), followed by a non-biological catalytic conversion to acrylic acid. Additionally, 3HP can be converted to other commodity chemicals including acrylamide and 1,3-propanediol [6]. One company, OPX Biotechnologies, has developed a bio-based technology for producing acrylic acid, via *Escherichia coli* fermentation of sugars to 3HP [7].

Cyanobacteria as an Alternative to Heterotrophic Bacteria

One of the concerns of using heterotrophic bacteria and yeast for fuel and chemical production is the use of food based commodities as feedstock. As the global population continues to grow and the cost of agricultural commodities continues to rise, an alternative route for biological production of commodity chemicals may be needed. An attractive alternative is to use cyanobacteria to convert $CO_2$ and light energy directly into chemical products. Using $CO_2$ rather than organic carbon as an input circumvents the problem of using agricultural commodities and could potentially decrease costs. Species of cyanobacteria are susceptible to genetic modification and have well studied metabolisms [8,9]. Recently, cyanobacteria have been engineered to produce a variety of chemicals and fuels including ethanol, hydrogen, isobutyraldehyde, isoprene, sugars, and fatty acids [10-14].

In order for cyanobacteria to be effective host systems for chemical production, they will have to produce the compound of interest in high titers and have improved resistance to end product toxicity. As presented below, a mutant strain of cyanobacteria was isolated with dramatically increased tolerance to acrylic acid and 3HP. This mutation was identified through exploring the role cyanobacteria play in metabolism of the marine sulfur compound dimethylsulfoniopropionate (DMSP).

Metabolism of the Sulfur Compound DMSP

DMSP is an organic sulfur compound produced by eukaryotic algae and plants that accounts for 1-10% of primary productivity in the oceans [16]. DMSP has been shown to act as an osmoprotectant, antioxidant, predator deterrent, and a sink for reduced sulfur in marine eukaryotic algae [17,18]. Upon its release into the water, DMSP is metabolized by bacterioplankton for use as a carbon and reduced sulfur source [19]. The catabolism of DMSP has the potential to supply 1-15% of total carbon demand and nearly all of the sulfur demand for these bacterial communities [20]. Additionally, cyanobacteria have been shown to account for 10-34% of total DMSP assimilation in light-exposed waters [21, 22].

DMSP is broken down through two major pathways. These pathways involve either direct cleavage of DMSP into dimethylsulfide (DMS) and acrylic acid or an initial demethylation followed by a cleavage reaction to form methanethiol and acrylic acid [16, 23-25]. Methanethiol is then used as a reduced sulfur source in methionine biosynthesis, while acrylic acid can be further metabolized into 3HP and used as a carbon source [26,27]. Additionally, release of DMS into the atmosphere from marine waters has been identified as a key intermediate in the cycling of terrestrial and marine sulfur pools [28]. While several genes have been identified in DMSP metabolism, none have been found in cyanobacteria.

Recent studies have shown that two different groups of cyanobacteria are involved in the metabolism of DMSP. These studies demonstrated that both *Synechococcus* and *Prochlorococcus* species are capable of assimilating radio labeled DMSP and methanethiol. In addition, four pure strains of *Synechococcus* were analyzed for DMSP assimilation. Two of the four strains were able to transport and assimilate DMSP, while another produced DMS [22]. Of the species of cyanobacteria currently being used in metabolic engineering, only one, *Synechococcus* sp. PCC 7002, is found in marine environments and potentially exposed to DMSP.

Example 1

Acrylic Acid is Produced from Incubation of DMSP with PCC 7002

Figure 2C:
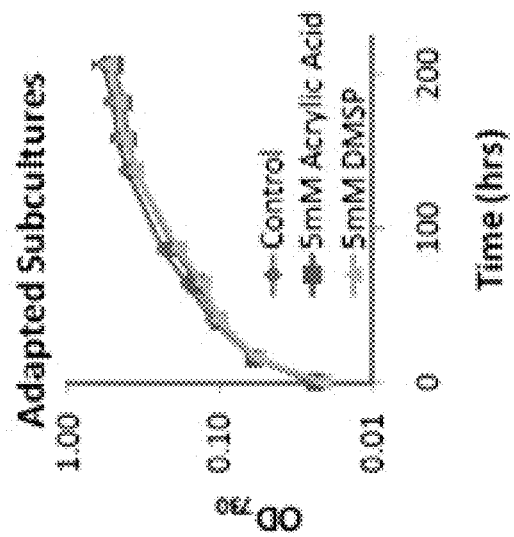
FIG. 2C. depicts growth of a mutant pool of *Synechococcus* sp. PCC 7002 at OD730 as a function of time in the presence of 5 mM dimethylsulfoniopropionate (DMSP) and 5 mM acrylic acid.
Figure 2B:
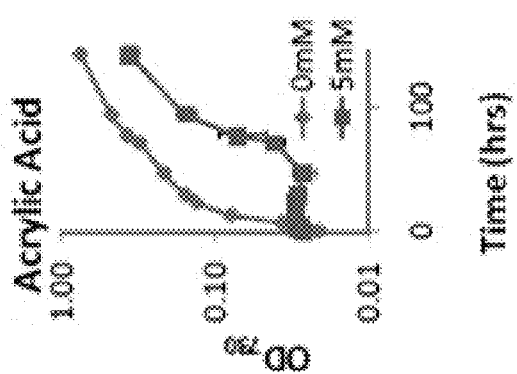
FIG. 2B. depicts growth of *Synechococcus* sp. PCC 7002 at OD730 as a function of time in the presence of 5 mM acrylic acid.
Figure 2A:
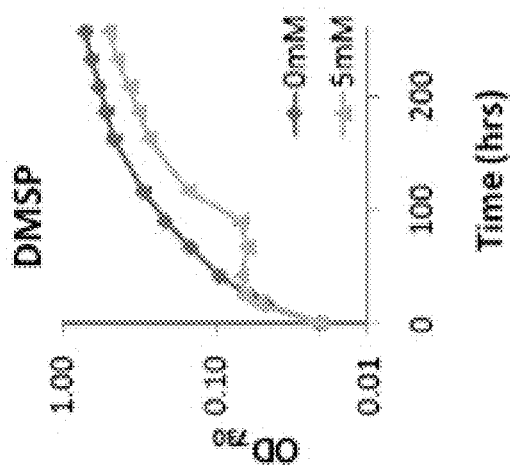
FIG. 2A. depicts growth of *Synechococcus* sp. PCC 7002 at OD730 as a function of time in the presence of 5 mM dimethylsulfoniopropionate (DMSP).
Figure 3:
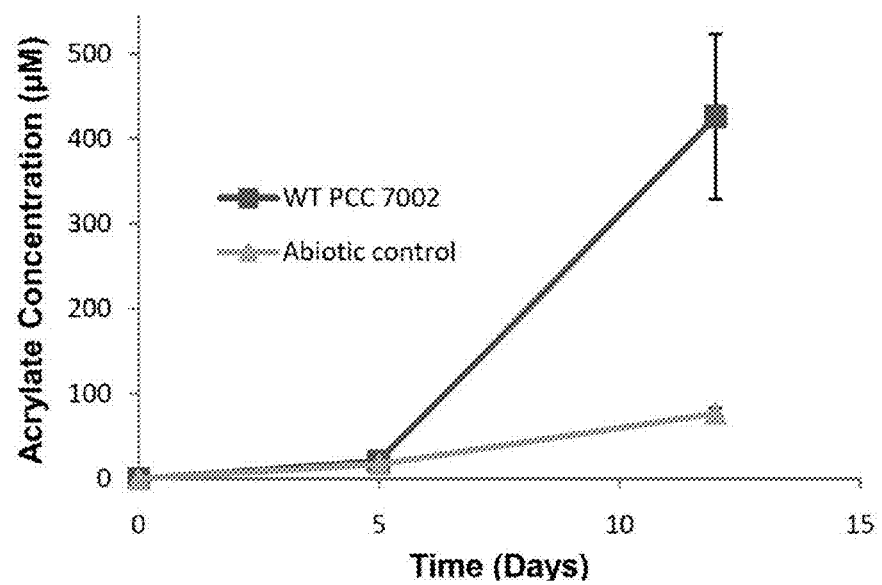
FIG. 3 depicts acrylate production from DMSP as a function of time for *Synechococcus* sp. PCC 7002 and an abiotic control.
Figure 4B:
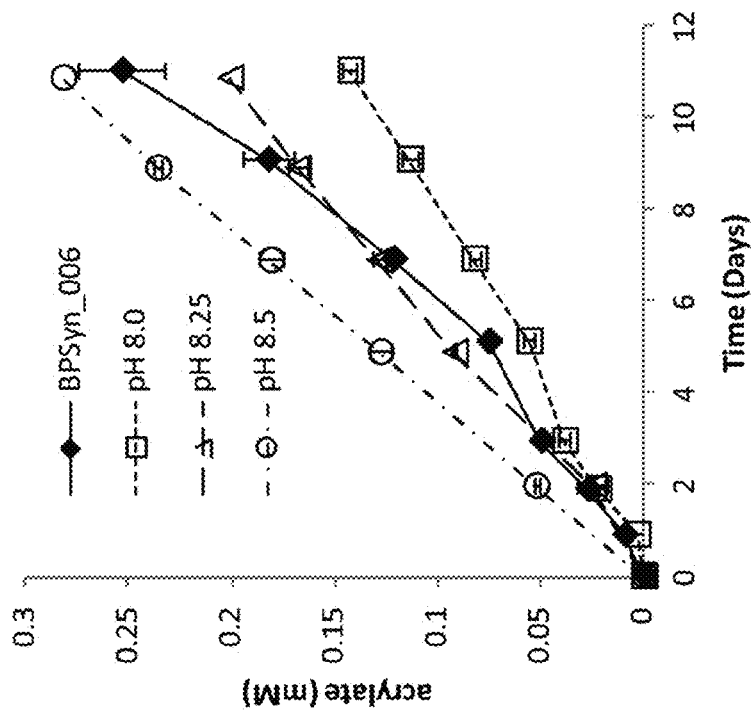
FIG. 4B depicts acrylic acid accumulation over time from cultivation of BPSyn_006 with 5 mM DMSP and abiotic controls with 5 mM DMSP at pH 8.0, 8.25, and 8.5. The rate of DMSP degradation to acrylic acid increases with an increase in pH.
Figure 4A:
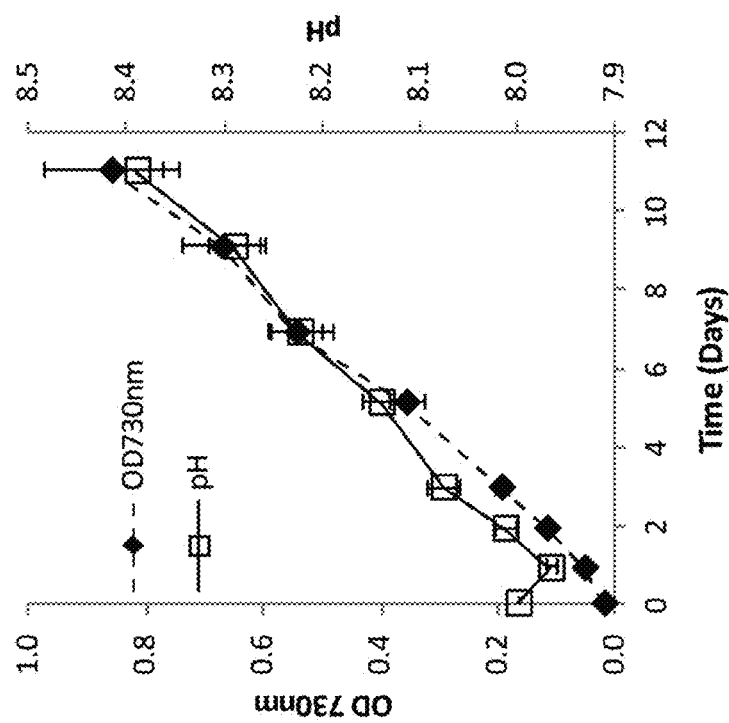
FIG. 4A depicts growth of BPSyn_006 (a ΔacsA strain of *Synechococcus* sp. PCC 7002 having a barcode sequence in place of the acsA gene (PCC 7002 acsA::BC)) and pH as a function of time in $CO_2$-limited conditions. Cultivation of BPSyn_006 with 5 mM DMSP under $CO_2$-limited conditions results in an increase in pH over time.

Metabolism of DMSP can result in the accumulation of several metabolites, including acrylic acid and 3HP, and may alter growth patterns due to its use as a carbon and sulfur source. PCC 7002 was cultured in the presence of 5 mM DMSP and analyzed for the presence of acrylic acid and 3HP. Growth was determined by monitoring OD730 while metabolic byproducts were measured through high pressure liquid chromatography (HPLC) and gas chromatography (GC). During incubation with DMSP, an increase in OD730 similar to a control culture was observed for several doubling events, followed by a delay in increased OD730 (FIG. 2A). HPLC analysis determined that during the initial growth period acrylic acid was being produced, although not at a rate significantly beyond an abiotic control (FIG. 3). However, extended incubation of PCC 7002 with DMSP resulted in an increase in acrylic acid concentrations beyond the abiotic control (FIG. 3). PCC 7002 does not contain genes with homology to those known to be involved in DMSP metabolism, but DMSP has been previously shown to slowly degrade to dimethylsulfide and acrylic acid at an alkaline pH [48,49]. The data presented in FIGS. 4A-B support a hypothesis that DMSP breakdown is abiotic and is enhanced by the increased pH resulting from cultivation of PCC 7002 under $CO_2$ limitation. The cultures in this study were not agitated or supplemented with bubbled air, creating a $CO_2$ limited environment. When grown in the presence of 5 mM acrylic acid, PCC 7002 exhibited a long lag followed by growth at a rate equal to the control (FIG. 2B). Both delays in increasing OD730 were linked by the presence of acrylic acid, suggesting that acrylic acid was causing growth inhibition. The eventual increase in OD730 in both cultures was due to spontaneous mutants within the population which were able to grow without inhibition. Sub-culturing of the mutant pool derived from wild type (WT) PCC 7002 grown with DMSP into medium containing acrylic acid resulted in no delay in growth (FIG. 2C). From these experiments it was concluded that DMSP incubated in the presence of PCC 7002 results in the production of acrylic acid, acrylic acid concentrations less than 5 mM are inhibitory, and spontaneous mutants can arise that are not inhibited by this concentration of acrylic acid.

Example 2

Acrylic Acid and 3HP Cause Toxicity at Low Concentrations

Accumulation of organic acid anions in the cytoplasm of bacteria has been shown to block metabolic pathways and arrest growth [32,33]. In addition to blocking metabolic pathways, high concentrations of organic acids have been shown to reduce the proton motive force through dissociation across the membrane [34]. Because of this, the toxicity of organic acids generally increases with the hydrophobicity of the compound [35]. The minimum inhibitory concentrations (MIC) for PCC 7002, *Synechococcus* sp. PCC 7942, and *Synechocystis* sp. PCC 6803 were determined for acrylic acid, 3HP, and propionic acid at a pH of about 8 (Table 1). In all three species, acrylic acid was significantly more toxic than propionic acid, which was more toxic than 3HP. Furthermore, the toxicity of acrylic acid (pKa 4.35) to PCC 7002 was shown to be pH dependent, with toxicity increasing with decreasing pH. The low MIC for acrylic acid explains why cultures grown with DMSP become growth inhibited. Cultures with DMSP only show growth inhibition when the accumulating acrylic acid concentration reaches inhibitory concentrations. This suggests that acrylic acid and not DMSP causes the inhibition of growth. The eventual increase in OD730 suggests that mutations can arise to overcome this inhibition.

TABLE 1

Minimum inhibitory concentration of organic acids in three cyanobacteria. Minimum inhibitory concentration is defined as the concentration at which no increase in $OD_{730}$ was observed. [1]Strain $A^+$ was isolated from an agar plate containing 5 mM acrylic acid.

| Species | Acrylic Acid | 3HP | Propionic Acid |
|---|---|---|---|
| Synechococcus sp. PCC 7942 | 3 µM | 2 mM | 250 µM |
| Synechocystis sp. PCC 6803 | 50 µM | No Data | 250 µM |
| Synechococcus sp. PCC 7002 | 25 µM | 10 mM | 4 mM |
| [1]PCC 7002 $A^+$ | 7 µM | No Data | No Data |

Example 3

A Mutation in an Acetyl-CoA Ligase Gene Increases Tolerance to Acrylic Acid and 3HP When a dense culture of PCC 7002 was plated onto solid medium containing acrylic acid, colonies resulting from spontaneous mutants uninhibited by acrylic acid were observed. The mutation frequency when selecting for growth on 50 µM acrylic acid was $7 \times 10^{-6}$. When selecting for growth on 5 mM acrylic acid, the mutation frequency was $4 \times 10^{-6}$. The mutation frequency is the frequency that a mutant with a given phenotype is found within the population of a culture. For example a mutation frequency of $1 \times 10^{-6}$ suggests that in a population of $1 \times 10^8$ cells, there are 100 mutants. The observed mutation frequencies are suggestive of a loss of function mutation. All mutants obtained from medium containing 50 µM acrylic acid were able to grow on 5 mM acrylic acid. In addition, these colonies were able to grow in media containing concentrations of propionic acid and 3HP that were above the WT PCC 7002 MIC values. One of the mutants, PCC 7002 $A^+$, was analyzed to determine to what degree the tolerance to organic acids had increased. MIC values for this strain are presented in Table 1. Tolerance to acrylic acid increased about 280-fold over WT PCC 7002 MIC values. Increased tolerance to 3HP and propionic acid was also observed (data not shown). Due to the increased tolerance to all three organic acids, the mutation may affect a gene that links the metabolism of acrylic acid, 3HP, and propionic acid.

In addition to looking at gene expression levels, the results from the RNA-sequencing experiment were used to identify mutations that resulted in increased tolerance to acrylic acid. An analysis for single nucleotide permutations (SNP) on the data set for each condition was performed. In order to identify potential mutation candidates, two basic assumptions were made. First, growth in cultures containing DMSP and acrylic acid would require the same mutation. Second, the mutation is a base pair change, not a deletion or insertion. From the SNP analysis, mutations in five candidate genes were identified. One of these candidates was annotated as an acetyl-CoA ligase (acsA). The mutation resulted in the change of a highly conserved tryptophan residue to a leucine (W49L) in Synechococcus sp. PCC 7002. The mutation changes an FWGE amino acid sequence in Synechococcus sp. PCC 7002 to an FLGE amino acid sequence. This mutation was a result of a G146T substitution in the acsA coding sequence. The mutation was present in ~60% of reads that aligned to this segment of the open reading frame in both the DMSP and acrylic acid cultures. Manual inspection of control alignment data determined that this allele was only present in cultures containing DMSP and acrylic acid. The correlate of W49 is conserved in the acsA of Escherichia coli (GenBank NP_418493.1) and Bacillus subtilis (GenBank NP_390846.1), among others, suggesting it is integral to a functional protein See, e.g., Table 2.

TABLE 2

Conservation of W49 and surrounding residues of Synechococcus sp. PCC 7002 acsA in acetyl-CoA ligases of E. coli K12 and P. fulva

| Organism | Gene | Protein Sequence | SEQ ID NO: |
|---|---|---|---|
| Synechococcus sp. PCC 7942 | acsA | F-W-G-E | Residues 48-51 of SEQ ID NO: 2 |
| E. coli K12 | Acetyl-CoA ligase | F-W-G-E | Residues 39-41 of SEQ ID NO: 9 |
| P. fulva | Acetyl-CoA ligase | F-W-G-E | Residues 38-41 of SEQ ID NO: 10 |

The W49L mutation residue resulted in an insoluble protein (data not shown) and, therefore, a non-functional protein. These data led to the hypothesis that loss of function of acsA would result in the observed increase in organic acid tolerance.

Without being limited by mechanism, it was hypothesized that the AcsA acetyl-CoA ligase may have a substrate specificity that would allow it to add a coenzyme A (CoA) to all three organic acids, and that the CoA bound acids or downstream metabolism of these CoA bound acids caused toxicity.

This hypothesis was tested by creating a knockout mutant of the acsA gene. This knockout was created by transforming wild type PCC 7002 with a DNA construct that would replace the acsA gene with an antibiotic resistance marker through homologous recombination. The resulting mutant, ΔacsA, was challenged with concentrations of acrylic acid, 3HP, and propionic acid above WT PCC 7002 MIC levels. In each case the ΔacsA mutant was able to grow without inhibition, including in the presence of >500 mM 3HP. Additionally, the ΔacsA mutant did not show any growth defects relative to wild type. These results show that loss of function of the acyl-CoA ligase increases the tolerance of PCC 7002 to acrylic acid and 3HP.

Figure 5:
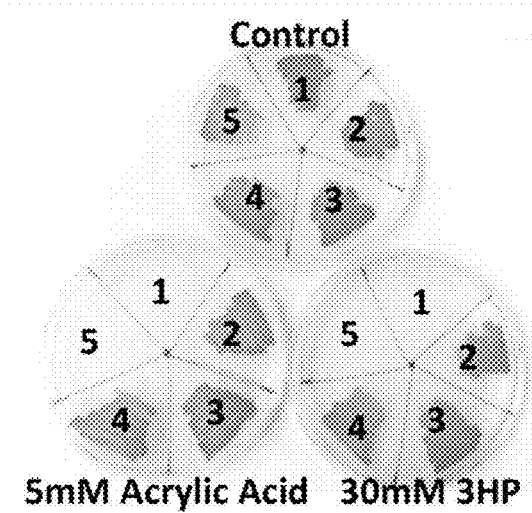
FIG. 5 depicts plating of wild-type *Synechococcus* sp. PCC 7002, a mutant generated from growth in the presence of acrylic acid, a ΔacsA mutant, a ΔacsA mutant comprising the pAQ1 plasmid containing acsAW49L, and a ΔacsA mutant comprising the pAQ1 plasmid containing acsA on media containing no organic acid, 5 mM acrylic acid, or 30 mM 3-hydroxypropionic acid (3HP).

To confirm this phenotype is the result of the deletion mutation, a complementation mutant was created by integrating a copy of acsA into a plasmid native to PCC 7002 ΔacsA. A corresponding mutant harboring a copy of acsA-W49L was also constructed. In the presence of acrylic acid, no strains harboring wild-type acsA were capable of growing while those harboring the mutant acsA were able to grow (FIG. 5).

In addition, the acsA gene was heterologously expressed in E. coli for protein purification and the substrate specificity was determined for AcsA in vitro (see below).

From these results, several conclusions can be drawn. DMSP is converted to acrylic acid by PCC 7002. Spontaneous mutations occur within the population that results in a drastically increased tolerance to acrylic acid, 3HP, and propionic acid. One mutation that can result in this phenotype is a loss of function or deletion of the acsA gene, which codes for an acetyl-CoA ligase.

Example 4

Deletion and Complementation Studies

Deletion and complementation studies were performed in various Synechococcus spp. and Synechocystis spp. The results are shown in Table 3. Replacement of the gene acsA in Synechococcus sp. PCC 7002 with an antibiotic resistance marker (aadA) resulted in a dramatic increase in tolerance to acrylic acid, 3-hydroxypropionic acid (3HP), and propionic acid. An identical level of increase was observed when acsA was replaced with a 20 base-pair barcode sequence. This phenotype was complemented in an acsA deletion strain by expression of acsA under the native promoter in another locus on the chromosome (glpK). Complementation resulted in the restored sensitivity to both acrylic acid and 3HP. The phenotype was only partially complemented upon expression of acsAW49L from the glpK locus, showing that the AW49L mutation does not result in a complete loss of AcsA activity.

Homologous genes were identified in the cyanobacteria Synechocystis sp. PCC 6803 (sll0542; SEQ ID NOS:3 and 4) and Synechococcus sp. PCC 7942 (SYNPCC7942_1342; SEQ ID NOS:5 and 6). Replacement of the gene sll0542 in PCC 6803 with an antibiotic resistance marker resulted in an increase in tolerance to acrylic acid similar to the deletion of acsA in PCC 7002. When selecting for growth of Synechocystis sp. PCC 6803 on 50 μM acrylic acid, the mutation frequency was $2 \times 10^{-6}$.

TABLE 3

Minimum inhibitory concentrations of organic acids

| Species | acrylic acid (mM) | 3-HP (mM) | Propionic acid (mM) |
|---|---|---|---|
| Synechococcus sp. PCC 7942 | 0.003 | 2 | 0.25 |
| Synechocystis sp. PCC 6803 | 0.050 | >35 | 0.25 |
| PCC 6803 sll0542::KmR | 70 | <50 | No Data |
| Synechococcus sp. PCC 7002 | 0.025 | 10 | 4 |
| PCC 7002 acsA::aadA | 70 | 260 | >400 |
| PCC 7002 acsA::BC* | 70 | 260 | No Data |
| PCC 7002 acsA:BC glpK::acsA aadA) | 0.015 | 15 | No Data |
| PCC 7002 acsA::BC glpK::acsAW49L aadA) | 7 | No Data | No Data |

*BC, 20 base-pair barcode

Example 5

Substrate Specificity of AcsA

The tolerance of PCC 7002 to acrylic acid and 3HP was dramatically increased by the deletion of the acetyl-CoA ligase gene (acsA). To obtain information regarding the AcsA-dependent toxicity, the substrate specificity of AcsA was determined.

Acyl-CoA ligase purification: Escherichia coli BL21 containing plasmid pET28b with acsA were grown in 50 mL of LB to an $OD_{600\ nm}$ of 0.6 and induced with 1 mM IPTG. The induced culture was shaken at 37° C. for 3 hrs. The culture was centrifuged and the resulting cell pellet was frozen at −20° C. The cell pellet was processed with Novagen Bug-Buster Protein Extraction Reagent (Part No. 70584-3). The resulting soluble protein fraction was used for His-tag purification using Ni-NTA agarose beads (Qiagen) and Pierce 0.8-mL centrifugation columns (Part No. 89868). Washes were done with 50 mM $NaH_2PO_4$, 300 mM NaCl, and 30 mM imidazole pH 8.0. The his-tagged protein was eluted with 50 mM $NaH_2PO_4$, 300 mM NaCl, and 250 mM imidazole pH 8.0. The insoluble fraction from the protein extraction was washed twice with BugBuster reagent followed by incubation with 400 μL 8M urea, 100 mM Tris-HCl, and 100 mM β-mercaptoethanol pH 8.2 for 30 min. The resulting solution was centrifuged at 16,000×g and the supernatant was collected. Protein fractions were run on a SDS-PAGE gel. His-tag purified protein fractions used in the acyl-CoA ligase assay were concentrated and buffered exchanged using an Amicon Ultra-4 centrifugation column. The buffer used for enzyme storage contained 0.1M $NaH_2PO_4$, 1 mM EDTA, and 10% v/v glycerol.

Figure 6:
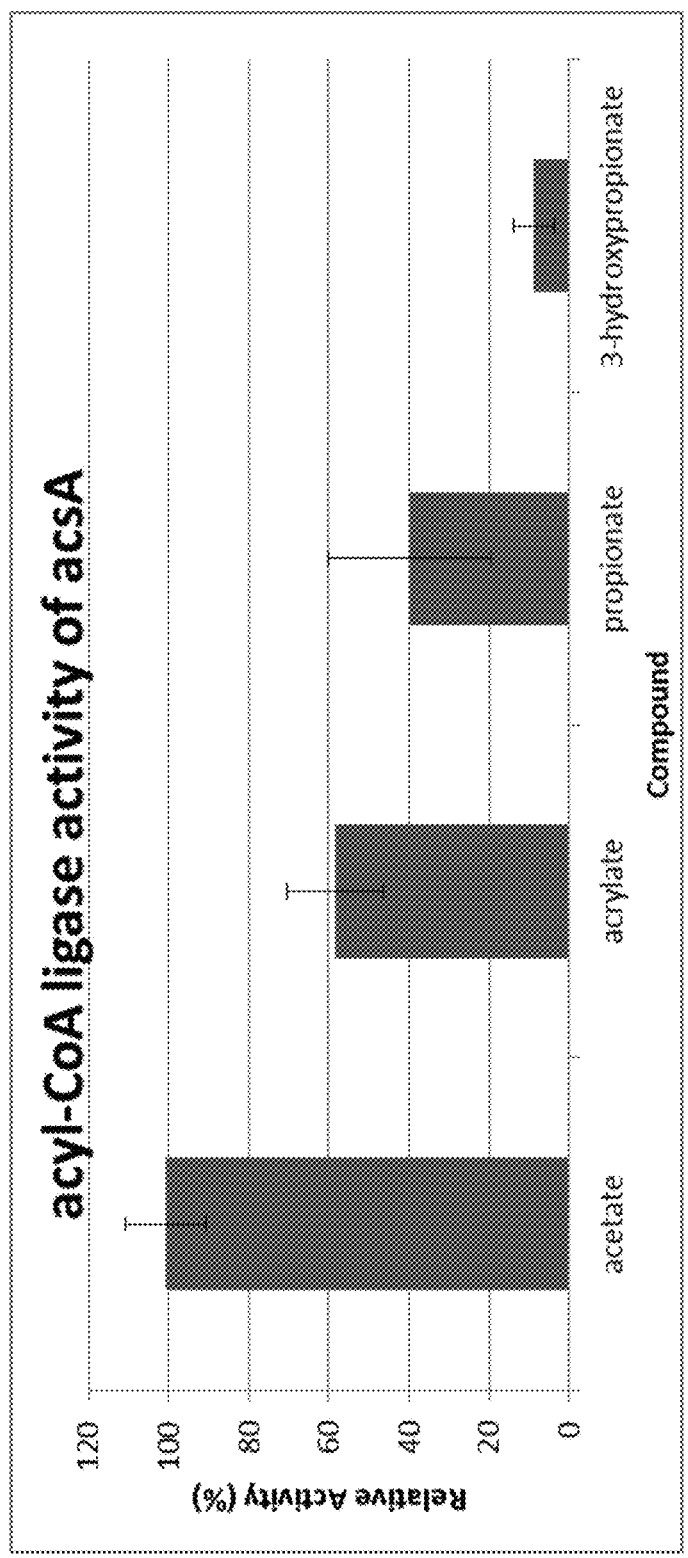
FIG. 6 depicts relative acyl-CoA ligase activity of AcsA for acetate, acrylate, propionate, and 3-hydroxypropionate (3HP).

Acyl-CoA ligase activity assay: Acyl-CoA ligase activity was determined by measuring the loss of free Coenzyme A (CoA) over time using Ellman's reagent. (Riddles P W, Blakeley R L, & Zerner B (1979) Ellman's reagent: 5,5'-dithiobis(2-nitrobenzoic acid)—a reexamination. Analytical Biochemistry 94(1):75-81.) The enzyme reaction contained 10 mM ATP, 8 mM $MgCl_2$, 3 mM CoA, 0.1 M $NaH_2PO_4$, 1 mM EDTA, and 2 mM of the organic acid species. The concentration of AcsA in the reaction was 500 nM. Relative activity was determined by the amount of CoA consumed in 4 min relative to an acetate control. As shown in FIG. 6, AcsA has an activity towards acetate, acrylic acid, propionate, and 3HP.

Example 6

Use of acsA as a Counter-Selection Marker

The sensitivity of PCC 7002 to acrylic acid due to the activity of AcsA allows for one to directly integrate DNA fragments into the acsA locus and select for acrylic acid tolerance. This method results in integration into the PCC 7002 without the use of an antibiotic resistance marker. The use of antibiotic resistance markers is limited by the number of markers available and their tendency to result in heterozygous strains. PCC 7002 carries between 4-6 copies of the chromosome and the use of resistance markers can result in strains with a mixture of native and modified chromosomes. Use of acsA as a counter-selection marker can quickly produce homozygous strains.

Figure 8A:
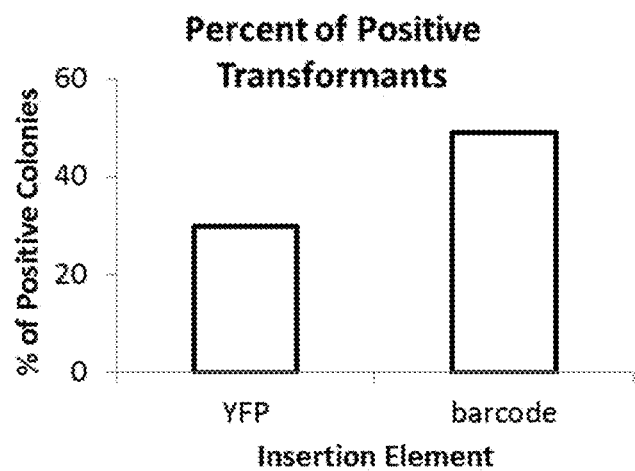
FIG. 8A depicts the percent of colonies positive for yellow fluorescent protein (YFP) or a barcode sequence resulting from use of acsA as a counter selection marker upon introducing the YFP or the barcode sequence into the chromosomal acsA locus of *Synechococcus* sp. PCC 7002.

The acsA gene was used as a counter-selection marker to introduce DNA fragments of interest into the acsA loci on the chromosome, thereby deleting acsA without leaving an antibiotic resistance marker. Wild type PCC 7002 was transformed with barcode DNA or DNA encoding yellow fluorescent protein (YFP), each flanked with 500 base-pair sequences homologous to regions directly 5' and 3' of acsA. The transformed culture was then plated on 50 μM acrylic acid. Colonies appeared after 3 days. The colonies were patched onto plates containing 50 μM acrylic acid and screened for the presence of the sequence of interest. Integration of the various sequences resulted in 30-50% of colonies being positive integrations. See FIG. 8A. Positive clones were streaked onto plates containing 10 mM acrylic acid. Colonies able to grow in the presence of 10 mM acrylic acid were homozygous for the integration. This method allows for fast and homozygous chromosomal integrations.

Figure 8B:
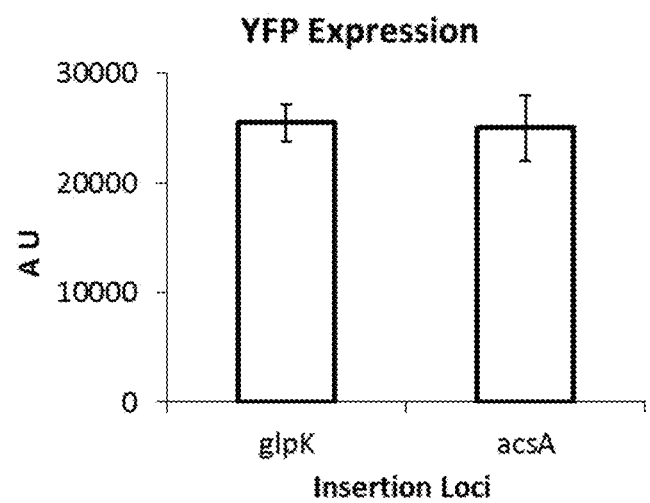
FIG. 8B depicts levels of YFP expression from cells in which YFP was introduced into the glpK chromosomal locus using acsA as a counter selection marker and cells in which YFP was introduced into the acsA chromosomal locus using acsA as a counter selection marker.

The acsA gene was also used as a counter selection marker to introduce DNA fragments of interest into other loci on the chromosome without leaving an antibiotic resistance marker. In an acsA deletion strain of PCC 7002, acsA along with an antibiotic resistance marker was introduced onto the chromosome into the gene glpK. See, e.g., PCC 7002 acsA:BC glpK::acsA aadA in Table 3. glpK was used as an insertion site because it is a pseudogene in PCC 7002 due to a frameshift mutation. The acsA-resistance marker was then replaced with yellow fluorescent protein (YFP) under the expression of a constitutive promoter. This resulted in a strain of PCC 7002 with YFP integrated onto the chromosome without a residual marker. YFP expressed from the glpK locus was shown to have an equal level of expression to YFP expressed from the acsA locus. See FIG. 8B. These experiments demonstrate the one can directly select for integration into the acsA locus and use acsA as a counter selection tool to make clean integrations elsewhere on the chromosome.

Example 7

Using a Mutant Strain of PCC 7002 with Increased Tolerance, Introduce a Pathway for Producing 3HP and Apply Metabolic Engineering Principles to Increase Titers While the ultimate goal is to produce acrylic acid through a single biological catalyst, no complete pathway has previously been demonstrated [5]. As an alternative, 3HP can be biologically derived and then catalytically converted to acrylic acid. A 3HP production pathway was introduced into PCC 7002 ΔacsA and its ability to produce 3HP from $CO_2$ and light energy was analyzed.

Express a Malonyl-CoA Reductase in PCC 7002

Figure 7:
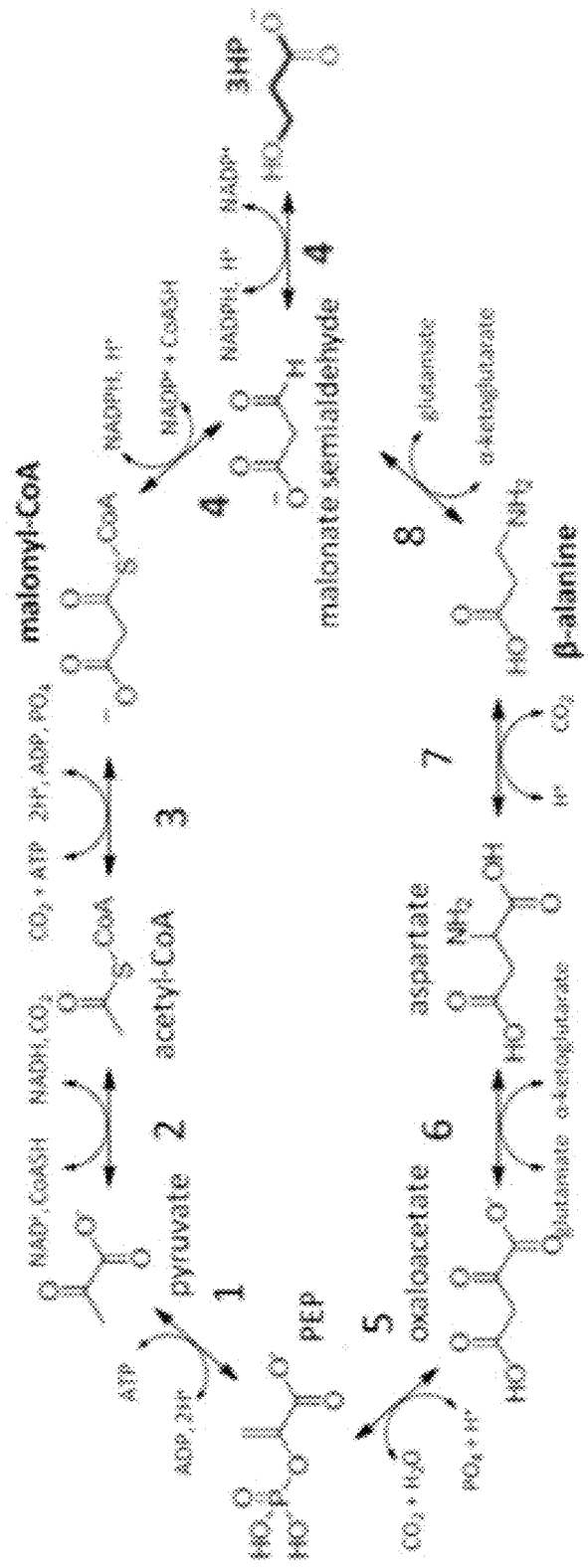
FIG. 7 depicts two 3HP-production pathways, wherein 1 represents pyruvate kinase, 2 represents pyruvate dehydrogenase, 3 represents acetyl-CoA carboxylase, 4 represents malonyl-CoA reductase, 5 represents phosphoenolpyruvate carboxylase, 6 represents aspartate aminotransferase, 7 represents aspartate decarboxylase, and 8 represents β-alanine/α-ketoglutarate aminotransferase.

FIG. 7 outlines two pathways for synthesizing 3HP from phosphoenolpyruvate (PEP). PEP is derived in cyanobacteria through the oxidation of glyceraldehyde 3-phosphate, a product of $CO_2$ assimilation. While both pathways would result in a cofactor imbalance, the route via malonyl-CoA balances out the NADPH derived from the light reactions of photosynthesis and results in the net production of 2 ATP and 2 NADH per 3HP. In order to introduce this pathway into PCC 7002, a malonyl-CoA reductase gene was heterologously expressed. Malonyl-CoA reductase from *Chloroflexus aurantiacus* was cloned into PCC 7002 ΔacsA [44]. *C. aurantiacus* is a phototrophic bacterium that produces 3HP as an intermediate in $CO_2$ fixation [45]. The malonyl-CoA reductase gene was introduced onto a native plasmid under a highly expressed promoter [46]. Integration onto a native plasmid rather than the chromosome ensured a higher copy number of the gene. The native plasmid is required for growth, ensuring that the plasmid was not lost [46]. After integration was confirmed, the ability of the strain to produce 3HP was determined through HPLC. Preliminary results have shown that expressing malonyl-CoA reductase in wild-type PCC 7002 and PCC 7002 ΔacsA confers the ability to produce 3HP on the order of 50 μM. Further experiments will be performed to determine if the ΔacsA strain has an advantage with respect to yield and growth rate. We predict that the ΔacsA strain has an advantage with respect to yield and growth rate.

The Strain Will be Engineered to Increase Titers

Several strategies can be employed to increase 3HP production. These include altering the expression of the malonyl-CoA reductase by changing the promoter, introducing additional copies onto the plasmid, and/or codon-optimizing the gene. Codon optimization will ensure that no rare codons exist in the coding sequence that would stall translation. Additionally, flux through this pathway can be increased by introducing highly expressed promoters in front of the acetyl-CoA carboxylase genes, thus increasing the pool of malonyl-CoA. Furthermore, a genome scale metabolic model can be used to predict genetic modifications that would provide additional flux through this pathway and correct cofactor imbalances [47]. These strategies will potentially increase titers of 3HP to be comparable with production systems using heterotrophic bacteria.

Conclusions from Examples

Increasing the tolerance of the cyanobacterium *Synechococcus* sp. PCC 7002 to the commodity chemicals acrylic acid and 3HP and increasing at least 3HP production through metabolic engineering make biological synthesis of these compounds from $CO_2$ a viable option.

REFERENCES

1. Keasling, J. D., *Manufacturing Molecules Through Metabolic Engineering*. Science, 2010. 330(6009): p. 1355-1358.
2. Chotani, G., et al., *The commercial production of chemicals using pathway engineering*. Biochimica et Biophysica Acta (BBA)—Protein Structure and Molecular Enzymology, 2000. 1543(2): p. 434-455.
3. Nakamura, C. E. and G. M. Whited, *Metabolic engineering for the microbial production of 1,3-propanediol*. Current Opinion in Biotechnology, 2003. 14(5): p. 454-459.
4. Bauer, W., *Acrylic Acid and Derivatives*. Kirk-Othmer Encyclopedia of Chemical Technology. 2000: John Wiley & Sons, Inc.
5. Straathof, A. J. J., et al., *Feasibility of acrylic acid production by fermentation*. Applied Microbiology and Biotechnology, 2005. 67(6): p. 727-734.
6. Bozell, J. J. and G. R. Petersen, *Technology development for the production of biobased products from biorefinery carbohydrates—the US Department of Energy's "Top 10" revisited*. Green Chemistry, 2010. 12(4): p. 539-554.
7. OPX nears commercial goal for bio-based acrylic acid Feb. 28, 2011; Available from: http://www.opxbiotechnologies.com/press/.
8. Thiel, T., *Genetic Analysis of Cyanobacteria*, in *The Molecular Biology of Cyanobacteria*, D. A. Bryant, Editor. 2004, Springer Netherlands. p. 581-611.
9. Ducat, D. C., J. C. Way, and P. A. Silver, *Engineering cyanobacteria to generate high-value products*. Trends in Biotechnology, 2011. 29(2): p. 95-103.
10. Angermayr, S. A., et al., *Energy biotechnology with cyanobacteria*. Current Opinion in Biotechnology, 2009. 20(3): p. 257-263.
11. Atsumi, S., W. Higashide, and J. C. Liao, *Direct photosynthetic recycling of carbon dioxide to isobutyraldehyde*. Nat Biotech, 2009. 27(12): p. 1177-1180.
12. Lindberg, P., S. Park, and A. Melis, *Engineering a platform for photosynthetic isoprene production in cyanobacteria, using Synechocystis as the model organism*. Metabolic Engineering, 2010. 12(1): p. 70-79.
13. Liu, X., J. Sheng, and R. Curtiss III, *Fatty acid production in genetically modified cyanobacteria*. Proceedings of the National Academy of Sciences, 2011.
14. Niederholtmeyer, H., et al., *Engineering Cyanobacteria To Synthesize and Export Hydrophilic Products*. Appl. Environ. Microbiol., 2010. 76(11): p. 3462-3466.
15. Kumar, K., et al., *Development of suitable photobioreactors for $CO_2$ sequestration addressing global warming using green algae and cyanobacteria*. Bioresource Technology, 2011. 102(8): p. 4945-4953.
16. Howard, E. C., et al., *Bacterial Taxa That Limit Sulfur Flux from the Ocean*. Science, 2006. 314(5799): p. 649-652.
17. Stefels, J., *Physiological aspects of the production and conversion of DMSP in marine algae and higher plants*. Journal of Sea Research, 2000. 43(3-4): p. 183-197.
18. Sunda, W., et al., *An antioxidant function for DMSP and DMS in marine algae*. Nature, 2002. 418(6895): p. 317-320.
19. Yoch, D. C., *Dimethylsulfoniopropionate: Its Sources, Role in the Marine Food Web, and Biological Degradation* to *Dimethylsulfide*. Appl. Environ. Microbiol., 2002. 68(12): p. 5804-5815.
20. Simó R., et al., *Coupled Dynamics of Dimethylsulfoniopropionate and Dimethylsulfide Cycling and the Microbial Food Web in Surface Waters of the North Atlantic*. Limnology and Oceanography, 2002. 47(1): p. 53-61.
21. Vila-Costa, M., et al., *Dimethylsulfoniopropionate Uptake by Marine Phytoplankton*. Science, 2006. 314(5799): p. 652-654.
22. Malmstrom, R. R., et al., *Dimethylsulfoniopropionate (DMSP) Assimilation by Synechococcus in the Gulf of Mexico and Northwest Atlantic Ocean*. Limnology and Oceanography, 2005. 50(6): p. 1924-1931.
23. González, J. M., et al., *Genetics and Molecular Features of Bacterial Dimethylsulfoniopropionate (DMSP) and Dimethylsulfide (DMS) Transformations*, in *Handbook of Hydrocarbon and Lipid Microbiology*, K. N. Timmis, Editor. 2010, Springer Berlin Heidelberg. p. 1201-1211.
24. Howard, E. C., et al., *Abundant and diverse bacteria involved in DMSP degradation in marine surface waters*. Environmental Microbiology, 2008. 10(9): p. 2397-2410.
25. Reisch, C. R., et al., *Novel pathway for assimilation of dimethylsulphoniopropionate widespread in marine bacteria*. Nature, 2011. 473(7346): p. 208-211.
26. Kiene, R. P., et al., *Dimethylsulfoniopropionate and Methanethiol Are Important Precursors of Methionine and Protein-Sulfur in Marine Bacterioplankton*. Appl. Environ. Microbiol., 1999. 65(10): p. 4549-4558.
27. Ansede, J. H., P. J. Pellechia, and D. C. Yoch, *Metabolism of Acrylate to beta—Hydroxypropionate and Its Role in Dimethylsulfoniopropionate Lyase Induction by a Salt Marsh Sediment Bacterium, Alcaligenes faecalis M3A*. Appl. Environ. Microbiol., 1999. 65(11): p. 5075-5081.
28. Simó, R., *Production of atmospheric sulfur by oceanic plankton: biogeochemical, ecological and evolutionary links*. Trends in Ecology & Evolution, 2001. 16(6): p. 287-294.
29. Ross, C. and K. L. V. Alstyne, *INTRASPECIFIC VARIATION IN STRESS-INDUCED HYDROGEN PEROXIDE SCAVENGING BY THE ULVOID MACROALGA ULVA LACTUCA1*. Journal of Phycology, 2007. 43(3): p. 466-474.
30. Latifi, A., M. Ruiz, and C.-C. Zhang, *Oxidative stress in cyanobacteria*. FEMS Microbiology Reviews, 2009. 33(2): p. 258-278.
31. Balasubramanian, R., et al., *Regulatory Roles for IscA and SufA in Iron Homeostasis and Redox Stress Responses in the Cyanobacterium Synechococcus sp. Strain PCC 7002*. J. Bacteriol., 2006. 188(9): p. 3182-3191.
32. Horswill, A. R., A. R. Dudding, and J. C. Escalante-Semerena, *Studies of Propionate Toxicity in Salmonella enterica Identify 2-Methylcitrate as a Potent Inhibitor of Cell Growth*. Journal of Biological Chemistry, 2001. 276 (22): p. 19094-19101.
33. Russell, J. B., *Another explanation for the toxicity of fermentation acids at low pH: anion accumulation versus uncoupling*. Journal of Applied Microbiology, 1992. 73(5): p. 363-370.
34. Chemington, C. A., et al., *Organic Acids: Chemistry, Antibacterial Activity and Practical Applications*, in *Advances in Microbial Physiology*, A. H. Rose and D. W. Tempest, Editors. 1991, Academic Press. p. 87-108.
35. Zaldivar, J. and L. O. Ingram, *Effect of organic acids on the growth and fermentation of ethanologenic Escherichia coli LY01*. Journal Name: Biotechnology and Bioengineering; Journal Volume: 66; Journal Issue: 4; Other Information: PBD: 1999, 1999: p. Medium: X; Size: page(s) 203-210.
36. Fridovich, I. and H. M. Hassan, *Paraquat and the exacerbation of oxygen toxicity*. Trends in Biochemical Sciences, 1979. 4(5): p. 113-115.
37. Sakamoto, T., V. B. Delgaizo, and D. A. Bryant, *Growth on Urea Can Trigger Death and Peroxidation of the Cyanobacterium Synechococcus sp. Strain PCC 7002*. Appl. Environ. Microbiol., 1998. 64(7): p. 2361-2366.
38. Steinke, M., et al., *Determinations of dimethylsulphoniopropionate (DMSP) lyase activity using headspace analysis of dimethylsulphide (DMS)*. Journal of Sea Research, 2000. 43(3-4): p. 233-244.
39. Hashimoto, Y., et al., *Nitrile Pathway Involving Acyl-CoA Synthetase*. Journal of Biological Chemistry, 2005. 280 (10): p. 8660-8667.
40. Kasuya, F., K. Igarashi, and M. Fukui, *Participation of a medium chain acyl-CoA synthetase in glycine conjugation of the benzoic acid derivatives with the electron-donating groups*. Biochemical Pharmacology, 1996. 51(6): p. 805-809.
41. MARUYAMA, K. and H. KITAMURA, *Mechanisms of Growth Inhibition by Propionate and Restoration of the Growth by Sodium Bicarbonate or Acetate in Rhodopseudomonas sphaeroides S*. Journal of Biochemistry, 1985. 98(3): p. 819-824.
42. Man, W.-J., et al., *The binding of propionyl-CoA and carboxymethyl-CoA to Escherichia coli citrate synthase*. Biochimica et Biophysica Acta (BBA)—Protein Structure and Molecular Enzymology, 1995. 1250(1): p. 69-75.
43. Boynton, Z. L., G. N. Bennett, and F. B. Rudolph, *Intracellular Concentrations of Coenzyme A and Its Derivatives from Clostridium acetobutylicum ATCC 824 and Their Roles in Enzyme Regulation*. Appl. Environ. Microbiol., 1994. 60(1): p. 39-44.
44. Hugler, M., et al., *Malonyl-Coenzyme A Reductase from Chloroflexus aurantiacus, a Key Enzyme of the 3-Hydroxypropionate Cycle for Autotrophic $CO_2$ Fixation*. J. Bacteriol., 2002. 184(9): p. 2404-2410.
45. Holo, H., *<i> Chloroflexus aurantiacus</i> secretes 3-hydroxypropionate, a possible intermediate in the assimilation of CO<sup>2</sup> and acetate*. Archives of Microbiology, 1989. 151(3): p. 252-256.
46. Xu, Y., et al., *Expression of Genes in Cyanobacteria: Adaptation of Endogenous Plasmids as Platforms for High-Level Gene Expression in <i> Synechococcus</i> sp. PCC 7002*, in *Photosynthesis Research Protocols*, R. Carpentier, Editor. 2011, Humana Press. p. 273-293.
47. Feist, A. M., et al., *Reconstruction of biochemical networks in microorganisms*. Nat Rev Micro, 2009. 7(2): p. 129-143.
48. Visscher, P. T., and H. van Gemerden. 1991. Production and Consumption of Dimethylsulfoniopropionate in Marine Microbial Mats. *Applied and Environmental Microbiology* 57:3237-3242.
49. Dacey, J. W. H., and N. V. Blough. 1987. Hydroxide decomposition of dimethylsulfoniopropionate to form dimethylsulfide. *Geophys. Res. Lett.* 14:1246-1249.

We claim:

1. An organic acid-tolerant microorganism comprising a modification that reduces or ablates AcsA activity or AcsA homolog activity in the microorganism, wherein tolerance to an organic acid selected from the group consisting of 3-hydroxypropionic acid (3HP), acrylic acid, and propionic acid is increased compared to a corresponding microorganism not comprising the modification, wherein the microorganism is a bacterium.

2. The microorganism of claim 1 wherein the modification is a genetic modification.

3. The microorganism of claim 1 wherein the modification is a genetic modification other than or in addition to one resulting in a W49L substitution in AcsA or a corresponding substitution in an AcsA homolog.

4. The microorganism of claim 1 wherein the microorganism is a cyanobacterium.

5. The microorganism of claim 1 wherein the microorganism is a cyanobacterium selected from the group consisting of Synechococcus sp., Prochlorococcus sp., Synechocystis sp., and Nostoc sp.

6. The microorganism of claim 1 wherein the tolerance to the organic acid is increased at least about 25-fold compared to the corresponding microorganism.

7. The microorganism of claim 1 wherein the microorganism is Synechococcus sp. and wherein the tolerance to the organic acid is selected from the group consisting of a minimum inhibitory concentration (MIC) of at least about 10 mM to acrylic acid, an MIC of at least about 100 mM to 3HP, and an MIC of at least about 200 mM to propionic acid.

8. The microorganism of claim 1 wherein the microorganism is capable of producing 3HP.

9. The microorganism of claim 1 wherein the microorganism includes at least one recombinant nucleic acid configured to overexpress a 3HP pathway enzyme.

10. A microbial culture comprising the microorganism of claim 1 and an amount of an organic acid.

11. A method of producing an organic acid comprising culturing a microorganism as recited in claim 1 in the presence of an amount of an organic acid selected from the group consisting of 3HP, acrylic acid, and propionic acid.

12. The microorganism of claim 9 wherein the at least one recombinant nucleic acid encoding the 3HP pathway enzyme includes a malonyl-CoA reductase gene.

13. The microorganism of claim 9 wherein the at least one recombinant nucleic acid encoding the 3HP pathway enzyme includes an acetyl-CoA carboxylase gene.

14. The microbial culture of claim 10 wherein the amount of the organic acid is selected from the group consisting of at least about 10 mM acrylic acid, at least about 100 mM 3HP, and at least about 200 mM propionic acid.

15. The method of claim 11 wherein the amount of the organic acid is selected from the group consisting of at least about 10 mM acrylic acid, at least about 100 mM 3HP, and at least about 200 mM propionic acid.

16. A method of using acsA or homolog thereof as a counter-selectable marker comprising:
 replacing an acsA or homolog thereof in a bacterium with a gene of interest; and
 selecting for the bacterium comprising the gene of interest with an amount of an organic acid effective to inhibit growth of bacteria harboring a functional acsA gene or homolog thereof.

17. The method of claim 16 wherein the acsA or homolog thereof is an acsA gene with at least one silent nucleic acid mutation that reduces background mutation frequency.

18. The method of claim 16 wherein the at least one silent nucleic acid mutation is selected from the group consisting of T144C and G150C in acsA from *Synechococcus* sp. PCC 7002.

19. The method of claim 16 wherein the selecting results in the bacterium being homozygous for the gene of interest.

* * * * *

SEQUENCE LISTING

<160> NUMBER OF SEQ ID NOS: 10

<210> SEQ ID NO 1
<211> LENGTH: 1965
<212> TYPE: DNA
<213> ORGANISM: Synechococcus PCC7002

<400> SEQUENCE: 1

| | | | | | | |
|---|---|---|---|---|---|---|
| atgtccgaac | aaaacattga | atccatcctc | caggagcagc | gccttttttc | gcctgcacca | 60 |
| gactttgctg | ccgaggccca | gatcaagagc | ttagaccagt | accaagccct | ctacgaccgg | 120 |
| gcgaaaaatg | accccgaagg | cttttggggg | gaactcgccg | aacaggaatt | ggaatggttt | 180 |
| gagaaatggg | acaaggtgct | cgattggcaa | ccgcccttcg | ccaaatggtt | tgtcaacggg | 240 |
| aaaattaaca | tttcctacaa | ttgcctcgac | cgtcatctca | aaacctggcg | caaaaataaa | 300 |
| gccgccctca | tctgggaagg | ggaacccggt | gactcccgta | ccctcaccta | tgcccagcta | 360 |
| caccacgagg | tctgccagtt | tgccaatgcg | atgaaaaagt | tgggcgtcaa | aaaaggcgat | 420 |
| cgcgtcggga | tttatatgcc | aatgatcccg | gaagccgtcg | ttgccctcct | cgcctgtgcc | 480 |
| cgcattggtg | cgccccatac | ggtgatattt | ggtggcttta | gtgccgaagc | cctccgcagt | 540 |
| cgcctcgaag | acgctgaagc | caaactggtg | atcaccgccg | acgggggctt | ccgcaaagat | 600 |
| aaagcggtac | ccctcaagga | tcaagtagat | gcggcgatcg | ccgatcacca | tgcccccagc | 660 |
| gttgagaatg | ttttggtcgt | tcaacgcacc | aaagagcctg | tccacatgga | agccgggcgg | 720 |
| gatcactggt | ggcatgattt | gcaaaaagaa | gtctccgctg | actgtcccgc | cgagccgatg | 780 |
| gatgccgaag | atatgctctt | catcctctat | accagcggca | ccacgggtaa | acccaagggc | 840 |
| gttgtccaca | ctacgggcgg | ttataatctc | tacacccata | taacgaccaa | gtggatcttt | 900 |
| gatctcaaag | atgatgacgt | gtattggtgt | ggtgctgatg | tgggttggat | caccggccac | 960 |
| agttacatta | cctatggccc | tctatctaac | ggggcaacgg | tcttaatgta | tgaaggcgca | 1020 |
| ccccgtccgt | ctaatcccgg | ttgctattgg | gaaattattc | aaaaatatgg | tgtcaccatt | 1080 |
| ttctatacgg | cacccacagc | gattcgggcc | tttatcaaaa | tgggtgaagg | catccccaat | 1140 |
| aaatatgaca | tgagttccct | gcgcctctta | ggaaccgtgg | gtgaaccgat | taacccagaa | 1200 |
| gcttggatgt | ggtaccaccg | ggtcattggt | ggcgaacgtt | gtcccattgt | tgatacatgg | 1260 |
| tggcaaacgg | aaaccggtgg | tgtgatgatt | acgcctttac | ccggtgcaac | tcccacaaaa | 1320 |
| cccggctcgg | caactcgtcc | ttttccgggg | attgtggcgg | atgtcgttga | ccttgatgga | 1380 |
| aattccgttg | gtgacaacga | aggcggctac | ctggtagtga | acaaccctg | gcctgggatg | 1440 |
| atgcgtactg | tttacggcaa | tcccgaacgc | ttccggtcta | cctattggga | gcacatcgcc | 1500 |
| ccgaaagatg | gacaatacct | ttatttcgca | ggtgacgggg | cacgccgtga | ccaagatggc | 1560 |
| tattttttgga | ttatgggtcg | cgtcgatgat | gtcttaaatg | tttcgggcca | tcgcctcggc | 1620 |
| accatggaag | tggaatcggc | cctcgtttcc | caccctgccg | tcgccgaagc | agccgtggtt | 1680 |
| ggaaagccag | atccggttaa | gggggaagag | gtgtttgcct | ttgtcaccct | tgagggcacc | 1740 |
| tacagtccga | gcgacgatct | cgtaacggaa | ctcaaggccc | atgtggtgaa | agaaattggg | 1800 |
| gcgatcgccc | gtccgggaga | aatccgtttt | gccgatgtaa | tgcccaaaac | ccgttctggg | 1860 |
| aagatcatgc | ggcgtttgtt | gcgaaaccta | gccgcaggtc | aggaaattgt | gggcgacacc | 1920 |
| tccaccctcg | aagaccgcag | cgtcctcgat | caactccggg | gctaa | | 1965 |

<210> SEQ ID NO 2

-continued

```
<211> LENGTH: 654
<212> TYPE: PRT
<213> ORGANISM: Synechococcus PCC7002

<400> SEQUENCE: 2
```

| | | | | | | | | | | | | | | |
|---|---|---|---|---|---|---|---|---|---|---|---|---|---|---|
| Met | Ser | Glu | Gln | Asn | Ile | Glu | Ser | Ile | Leu | Gln | Glu | Gln | Arg | Leu | Phe |
| 1 | | | | 5 | | | | | 10 | | | | | 15 | |
| Ser | Pro | Ala | Pro | Asp | Phe | Ala | Ala | Glu | Ala | Gln | Ile | Lys | Ser | Leu | Asp |
| | | | 20 | | | | | 25 | | | | | 30 | | |
| Gln | Tyr | Gln | Ala | Leu | Tyr | Asp | Arg | Ala | Lys | Asn | Asp | Pro | Glu | Gly | Phe |
| | | | 35 | | | | 40 | | | | | 45 | | | |
| Trp | Gly | Glu | Leu | Ala | Glu | Gln | Glu | Leu | Glu | Trp | Phe | Glu | Lys | Trp | Asp |
| | 50 | | | | | 55 | | | | | 60 | | | | |
| Lys | Val | Leu | Asp | Trp | Gln | Pro | Pro | Phe | Ala | Lys | Trp | Phe | Val | Asn | Gly |
| 65 | | | | | 70 | | | | | 75 | | | | | 80 |
| Lys | Ile | Asn | Ile | Ser | Tyr | Asn | Cys | Leu | Asp | Arg | His | Leu | Lys | Thr | Trp |
| | | | | 85 | | | | | 90 | | | | | 95 | |
| Arg | Lys | Asn | Lys | Ala | Ala | Leu | Ile | Trp | Glu | Gly | Glu | Pro | Gly | Asp | Ser |
| | | | 100 | | | | | 105 | | | | | 110 | | |
| Arg | Thr | Leu | Thr | Tyr | Ala | Gln | Leu | His | His | Glu | Val | Cys | Gln | Phe | Ala |
| | | | 115 | | | | 120 | | | | | 125 | | | |
| Asn | Ala | Met | Lys | Lys | Leu | Gly | Val | Lys | Lys | Gly | Asp | Arg | Val | Gly | Ile |
| | 130 | | | | | 135 | | | | | 140 | | | | |
| Tyr | Met | Pro | Met | Ile | Pro | Glu | Ala | Val | Val | Ala | Leu | Leu | Ala | Cys | Ala |
| 145 | | | | | 150 | | | | | 155 | | | | | 160 |
| Arg | Ile | Gly | Ala | Pro | His | Thr | Val | Ile | Phe | Gly | Gly | Phe | Ser | Ala | Glu |
| | | | | 165 | | | | | 170 | | | | | 175 | |
| Ala | Leu | Arg | Ser | Arg | Leu | Glu | Asp | Ala | Glu | Ala | Lys | Leu | Val | Ile | Thr |
| | | | 180 | | | | | 185 | | | | | 190 | | |
| Ala | Asp | Gly | Gly | Phe | Arg | Lys | Asp | Lys | Ala | Val | Pro | Leu | Lys | Asp | Gln |
| | | | 195 | | | | | 200 | | | | | 205 | | |
| Val | Asp | Ala | Ala | Ile | Ala | Asp | His | His | Ala | Pro | Ser | Val | Glu | Asn | Val |
| | 210 | | | | | 215 | | | | | 220 | | | | |
| Leu | Val | Val | Gln | Arg | Thr | Lys | Glu | Pro | Val | His | Met | Glu | Ala | Gly | Arg |
| 225 | | | | | 230 | | | | | 235 | | | | | 240 |
| Asp | His | Trp | Trp | His | Asp | Leu | Gln | Lys | Glu | Val | Ser | Ala | Asp | Cys | Pro |
| | | | | 245 | | | | | 250 | | | | | 255 | |
| Ala | Glu | Pro | Met | Asp | Ala | Glu | Asp | Met | Leu | Phe | Ile | Leu | Tyr | Thr | Ser |
| | | | 260 | | | | | 265 | | | | | 270 | | |
| Gly | Thr | Thr | Gly | Lys | Pro | Lys | Gly | Val | Val | His | Thr | Thr | Gly | Gly | Tyr |
| | | | 275 | | | | | 280 | | | | | 285 | | |
| Asn | Leu | Tyr | Thr | His | Ile | Thr | Thr | Lys | Trp | Ile | Phe | Asp | Leu | Lys | Asp |
| | 290 | | | | | 295 | | | | | 300 | | | | |
| Asp | Asp | Val | Tyr | Trp | Cys | Gly | Ala | Asp | Val | Gly | Trp | Ile | Thr | Gly | His |
| 305 | | | | | 310 | | | | | 315 | | | | | 320 |
| Ser | Tyr | Ile | Thr | Tyr | Gly | Pro | Leu | Ser | Asn | Gly | Ala | Thr | Val | Leu | Met |
| | | | | 325 | | | | | 330 | | | | | 335 | |
| Tyr | Glu | Gly | Ala | Pro | Arg | Pro | Ser | Asn | Pro | Gly | Cys | Tyr | Trp | Glu | Ile |
| | | | 340 | | | | | 345 | | | | | 350 | | |
| Ile | Gln | Lys | Tyr | Gly | Val | Thr | Ile | Phe | Tyr | Thr | Ala | Pro | Thr | Ala | Ile |
| | | | 355 | | | | | 360 | | | | | 365 | | |
| Arg | Ala | Phe | Ile | Lys | Met | Gly | Glu | Gly | Ile | Pro | Asn | Lys | Tyr | Asp | Met |
| | 370 | | | | | 375 | | | | | 380 | | | | |
| Ser | Ser | Leu | Arg | Leu | Leu | Gly | Thr | Val | Gly | Glu | Pro | Ile | Asn | Pro | Glu |
| 385 | | | | | 390 | | | | | 395 | | | | | 400 |

```
Ala Trp Met Trp Tyr His Arg Val Ile Gly Gly Glu Arg Cys Pro Ile
                405                 410                 415

Val Asp Thr Trp Trp Gln Thr Glu Thr Gly Gly Val Met Ile Thr Pro
            420                 425                 430

Leu Pro Gly Ala Thr Pro Thr Lys Pro Gly Ser Ala Thr Arg Pro Phe
        435                 440                 445

Pro Gly Ile Val Ala Asp Val Val Asp Leu Asp Gly Asn Ser Val Gly
    450                 455                 460

Asp Asn Glu Gly Gly Tyr Leu Val Val Lys Gln Pro Trp Pro Gly Met
465                 470                 475                 480

Met Arg Thr Val Tyr Gly Asn Pro Glu Arg Phe Arg Ser Thr Tyr Trp
                485                 490                 495

Glu His Ile Ala Pro Lys Asp Gly Gln Tyr Leu Tyr Phe Ala Gly Asp
            500                 505                 510

Gly Ala Arg Arg Asp Gln Asp Gly Tyr Phe Trp Ile Met Gly Arg Val
        515                 520                 525

Asp Asp Val Leu Asn Val Ser Gly His Arg Leu Gly Thr Met Glu Val
    530                 535                 540

Glu Ser Ala Leu Val Ser His Pro Ala Val Ala Glu Ala Ala Val Val
545                 550                 555                 560

Gly Lys Pro Asp Pro Val Lys Gly Glu Glu Val Phe Ala Phe Val Thr
                565                 570                 575

Leu Glu Gly Thr Tyr Ser Pro Ser Asp Asp Leu Val Thr Glu Leu Lys
            580                 585                 590

Ala His Val Val Lys Glu Ile Gly Ala Ile Ala Arg Pro Gly Glu Ile
        595                 600                 605

Arg Phe Ala Asp Val Met Pro Lys Thr Arg Ser Gly Lys Ile Met Arg
    610                 615                 620

Arg Leu Leu Arg Asn Leu Ala Ala Gly Gln Glu Ile Val Gly Asp Thr
625                 630                 635                 640

Ser Thr Leu Glu Asp Arg Ser Val Leu Asp Gln Leu Arg Gly
                645                 650

<210> SEQ ID NO 3
<211> LENGTH: 1962
<212> TYPE: DNA
<213> ORGANISM: Synechocystis PCC6803

<400> SEQUENCE: 3
atgtcagata ccattgaatc catcctgcag gaagagcgac tgtttgatcc ccctacagaa      60
tttagtgagc gggcttacgt gcgtagtggg cgggagtatg agcaactgta cagccgggcg     120
gccagcaatc cggagaagtt ttggggtgag ctggcggagc aggaattaca ttggtttaaa     180
aaatgggacc aggttttgga ttggcaacct ccctttgcga atggtttgt gggggggtcag     240 ttaaatattt cccataactg tttggatcgg cacttaacca cctggcggcg caataaggcg     300
gccattattt gggaggggga accgggagat tcccggataa ttacctatgc ccaactccat     360
cgggaagtgt gtcagtttgc caatgccctg aaaagtttag gcgtgcaaaa aggtgatcgg     420
gtagcaattt atctgcccat gattcccgaa gcggcgatca ccatgttggc ctgttcccgt     480
atcggtgcgc cccatagtgt tgtgtttggt gggtttagtg cggaagccct gcgggatcga     540
ttagtggatg ctgaagccaa attggtcata actgccgacg gtggttttcg taaagataag     600
gcgatcgccc tgaagcagga agtggataag gccctggaac acggtgcccc cagcgtggaa     660
aacgtcatcg tcgtgcaaag aactaaagcc gatgtgacca tgacggcggg acgggaccac     720
```

-continued

```
tggtggcacg aactccaacc tcaacagtcg gcccattgcc cagcggaacc catagacagt      780
gaagatatgc tgtttattct ctacacctct ggcagtactg gcaaaccaaa aggcgtggtc      840
cacaccaccg ggggttacaa cctttacacc cacatgacca ccaaatggat ctttgacctc      900
aaagatacgg acgtttattg gtgtaccgct gatgtgggtt ggattacggg ccacagctac      960
attgtttacg gcccctgtc caacggtgca caacggtaa tgtatgaagg ggtgccccgc       1020
ccctccaacc ccggttgttt tgggacgta attgaaaggt atggggtgaa tattttctac      1080
accgccccca ccgccatccg agcctttatt cgcatggggg aagccgtacc caacgccagg     1140
gatttatcct ctctccgttt actgggcact gtggggggaac ccattaaccc cgaagcttgg    1200
atgtggtacc accgggtcat ggcggcggt aaatgcccca ttgtcgatac ctggtggcaa      1260
acggaaaccg gcggcattat gctcactccc ctacctggag ctatccctac caaacccggt     1320
tcttgtacca aaccttttcc cggcattgtg gcggaaattg ttgatttaga tggcaatccc     1380
gtcgagtcag accaagggg cttttttagtg attaaacaac cttggcccag catgattcgg    1440
gatgtgtacg gcgacaccga tcgcttccgc catacctatt gggaacatat tcaacccaag    1500
gagggacaat atctctactt tgctggggac ggggcccgcc gggataaaga cggttatttt    1560
tgggtcatgg gccgggtgga tgatgtgatt aatgtctctg gtcaccgttt aggcactatg    1620
gaaattgaat cggctttggt ttcccatccc ctcgtagcgg aagcggcggt ggtgggtcgc    1680
cccgatgaat tgactgggga agccattttc gcctttgttt ctctggaggg taacgctgaa    1740
cccagtgaag agttgaaaaa agatttggtc aagcacgtca ctgaagaaat tggggcgatc   1800
gccaggccag cggaaatccg tttcaccgat gtgttaccca aaacccgttc cggcaaaatt    1860
atgcgtcgtc tgttgcggag tttagcctcc gggcaggaaa tttccgggga cacttccacc     1920
ctggaggacc ggacagtgct ggacaaatta cgggagggct aa                        1962

<210> SEQ ID NO 4
<211> LENGTH: 653
<212> TYPE: PRT
<213> ORGANISM: Synechocystis PCC6803

<400> SEQUENCE: 4

Met Ser Asp Thr Ile Glu Ser Ile Leu Gln Glu Glu Arg Leu Phe Asp
1               5                   10                  15

Pro Pro Thr Glu Phe Ser Glu Arg Ala Tyr Val Arg Ser Gly Arg Glu
            20                  25                  30

Tyr Glu Gln Leu Tyr Ser Arg Ala Ala Ser Asn Pro Glu Lys Phe Trp
        35                  40                  45

Gly Glu Leu Ala Glu Gln Glu Leu His Trp Phe Lys Lys Trp Asp Gln
    50                  55                  60

Val Leu Asp Trp Gln Pro Pro Phe Ala Lys Trp Phe Val Gly Gly Gln
65                  70                  75                  80

Leu Asn Ile Ser His Asn Cys Leu Asp Arg His Leu Thr Thr Trp Arg
                85                  90                  95

Arg Asn Lys Ala Ala Ile Ile Trp Glu Gly Pro Gly Asp Ser Arg
            100                 105                 110

Ile Ile Thr Tyr Ala Gln Leu His Arg Glu Val Cys Gln Phe Ala Asn
        115                 120                 125

Ala Leu Lys Ser Leu Gly Val Gln Lys Gly Asp Arg Val Ala Ile Tyr
    130                 135                 140

Leu Pro Met Ile Pro Glu Ala Ala Ile Thr Met Leu Ala Cys Ser Arg
145                 150                 155                 160
```

```
Ile Gly Ala Pro His Ser Val Val Phe Gly Phe Ser Ala Glu Ala
            165                 170                 175

Leu Arg Asp Arg Leu Val Asp Ala Glu Ala Lys Leu Val Ile Thr Ala
            180                 185                 190

Asp Gly Gly Phe Arg Lys Asp Lys Ala Ile Ala Leu Lys Gln Glu Val
            195                 200                 205

Asp Lys Ala Leu Glu His Gly Ala Pro Ser Val Glu Asn Val Ile Val
210                 215                 220

Val Gln Arg Thr Lys Ala Asp Val Thr Met Thr Ala Gly Arg Asp His
225                 230                 235                 240

Trp Trp His Glu Leu Gln Pro Gln Gln Ser Ala His Cys Pro Ala Glu
            245                 250                 255

Pro Ile Asp Ser Glu Asp Met Leu Phe Ile Leu Tyr Thr Ser Gly Ser
            260                 265                 270

Thr Gly Lys Pro Lys Gly Val Val His Thr Thr Gly Gly Tyr Asn Leu
            275                 280                 285

Tyr Thr His Met Thr Thr Lys Trp Ile Phe Asp Leu Lys Asp Thr Asp
            290                 295                 300

Val Tyr Trp Cys Thr Ala Asp Val Gly Trp Ile Thr Gly His Ser Tyr
305                 310                 315                 320

Ile Val Tyr Gly Pro Leu Ser Asn Gly Ala Thr Thr Val Met Tyr Glu
            325                 330                 335

Gly Val Pro Arg Pro Ser Asn Pro Gly Cys Phe Trp Asp Val Ile Glu
            340                 345                 350

Arg Tyr Gly Val Asn Ile Phe Tyr Thr Ala Pro Thr Ala Ile Arg Ala
            355                 360                 365

Phe Ile Arg Met Gly Glu Ala Val Pro Asn Ala Arg Asp Leu Ser Ser
            370                 375                 380

Leu Arg Leu Leu Gly Thr Val Gly Glu Pro Ile Asn Pro Glu Ala Trp
385                 390                 395                 400

Met Trp Tyr His Arg Val Ile Gly Gly Gly Lys Cys Pro Ile Val Asp
            405                 410                 415

Thr Trp Trp Gln Thr Glu Thr Gly Gly Ile Met Leu Thr Pro Leu Pro
            420                 425                 430

Gly Ala Ile Pro Thr Lys Pro Gly Ser Cys Thr Lys Pro Phe Pro Gly
            435                 440                 445

Ile Val Ala Glu Ile Val Asp Leu Asp Gly Asn Pro Val Glu Ser Asp
450                 455                 460

Gln Gly Gly Phe Leu Val Ile Lys Gln Pro Trp Pro Ser Met Ile Arg
465                 470                 475                 480

Asp Val Tyr Gly Asp Thr Asp Arg Phe Arg His Thr Tyr Trp Glu His
            485                 490                 495

Ile Gln Pro Lys Glu Gly Gln Tyr Leu Tyr Phe Ala Gly Asp Gly Ala
            500                 505                 510

Arg Arg Asp Lys Asp Gly Tyr Phe Trp Val Met Gly Arg Val Asp Asp
            515                 520                 525

Val Ile Asn Val Ser Gly His Arg Leu Gly Thr Met Glu Ile Glu Ser
530                 535                 540

Ala Leu Val Ser His Pro Leu Val Ala Glu Ala Val Val Gly Arg
545                 550                 555                 560

Pro Asp Glu Leu Thr Gly Glu Ala Ile Phe Ala Phe Val Ser Leu Glu
            565                 570                 575

Gly Asn Ala Glu Pro Ser Glu Glu Leu Lys Lys Asp Leu Val Lys His
```

```
                580             585              590
Val Thr Glu Glu Ile Gly Ala Ile Ala Arg Pro Ala Glu Ile Arg Phe
                    595              600             605

Thr Asp Val Leu Pro Lys Thr Arg Ser Gly Lys Ile Met Arg Arg Leu
        610             615             620

Leu Arg Ser Leu Ala Ser Gly Gln Glu Ile Ser Gly Asp Thr Ser Thr
625             630             635             640

Leu Glu Asp Arg Thr Val Leu Asp Lys Leu Arg Glu Gly
                645             650

<210> SEQ ID NO 5
<211> LENGTH: 1971
<212> TYPE: DNA
<213> ORGANISM: Synechococcus PCC7942

<400> SEQUENCE: 5
```

| | | | | | |
|---|---|---|---|---|---|
| atgagccagc | caacgatcga | gtcgatcctc | caagagaagc | gggttttttcc | tccctcggca | 60 |
| gaatttgcca | gtgcggcgcg | aatcaatccc | gaagcgtacg | aagcgctctg | ccagaaagcg | 120 |
| gcggccgatc | cggtggcttt | tgggggcgaa | ttggcagctc | aggagctgga | ctggtttgag | 180 |
| ccttggcaac | agacgctgga | ctggagcaat | ccgccgtttg | cgaagtggtt | tgtcggtggc | 240 |
| aaactcaata | tttcccacaa | ctgcctcgat | cgccacttga | cgacttggcg | caaaaataaa | 300 |
| gcggcgatta | tctgggaagg | cgaacccggt | gactcacgga | cgctgaccta | cgcgcaactg | 360 |
| catcgcgagg | tctgtcagtt | cgccaacgtg | ctcaaatcct | tgggcattca | aaaaggtgat | 420 |
| gtcgttggcg | tttacatgcc | gatgattccc | gaagcggcga | tcgccatgct | ggcctgtgcg | 480 |
| cggattggcg | cagtgcatag | cgttgtcttt | gggggcttta | gtgcggaagc | actgcgcgat | 540 |
| cgcttggtgg | atgccaagc | caagctggtt | gtcacgcgcg | gatggtggctg | gcgcaaagat | 600 |
| gcgatcgtgc | ccctcaagga | ttctgttgat | caagccctgg | aaggcaatgc | ctgccccagc | 660 |
| gtccagcatg | tcctcgtggt | ggaacggacg | aagcaagaca | tccacatgga | accggggcgc | 720 |
| gaccattggt | ggcatgagct | gcaacagacc | gtcagcgcta | cctgtccggc | ggagccgatg | 780 |
| gacagcgaag | atctgctctt | cgtgctctac | acctccggta | gcaccggcaa | acccaagggt | 840 |
| gtcgtccaca | ccaccggcgg | ctacaacctc | tacgcccaca | tcaccaccca | gtggactttt | 900 |
| gacctgcagg | ataccgatgt | ctactggtgt | acggcggacg | tcggctggat | taccggtcac | 960 |
| agctacatcg | tctacgggcc | gctctccaac | ggtgcgacca | cactgatgta | tgagggtgcc | 1020 |
| ccccgcgctt | ctaatcccgg | ttgcttctgg | gatgtgattg | aaaagtatgg | cgttacgacc | 1080 |
| ttctacacag | ccccaacagc | gatccgcgcc | ttcatcaaaa | tgggtgagca | gcatcccgcc | 1140 |
| gctcgcgacc | tctcctcatt | gcgactgttg | gcaccgtcg | gagagcccat | caatcccgaa | 1200 |
| gcttggatct | ggtatcaccg | cgtcattggt | ggcgatcgct | gcccgattgt | cgatacctgg | 1260 |
| tggcagaccg | aaacgggcgg | ccatatgatt | acgtcgctgc | cggagccgt | gccgaccaaa | 1320 |
| ccgggctctg | ccactaaacc | tttcccgggc | atcttggcag | acgttgtcga | tctggatggg | 1380 |
| cgatcggtgc | cggataacga | aggtggctac | ttggtgattc | gccatccttg | gccaggcatg | 1440 |
| atgcgcacgg | tctacggcga | tcccgatcgc | ttccgtcgca | cctattggga | gcatattcct | 1500 |
| ccgcaaaatg | ccagtatct | ctacttcgcc | ggcgatggcg | cgcgccgcga | tgccgatggc | 1560 |
| tatttctggg | tgatggggcg | cgtcgatgac | gtgatcaatg | tctcaggtca | ccgtctcggc | 1620 |
| acgatggaaa | ttgagtcggc | cttggtctcc | catccggcag | ttgccgaagc | tgcagttgtc | 1680 |
| ggtcggcctg | acgatctcaa | aggtgaaggc | attgttgctt | tcatcacgct | ggaatcgggc | 1740 |

-continued

```
attgagactg gcgatgagtt agttaaagac ctgaagaaac acgtcgccca agaaattggc    1800
gcgatcgctc gtcccgatga aattcgcttc agtgaggcgc tgcccaaaac gcgatcgggc    1860
aagattatgc ccgtctgtt gcgcagtctc gccgctggtc aagaagtttc gggcgacact    1920
tccaccttgg aagatcgctc ggtgctcgat aagctgcgtc aaggcactta g             1971
```

```
<210> SEQ ID NO 6
<211> LENGTH: 656
<212> TYPE: PRT
<213> ORGANISM: Synechococcus PCC7942

<400> SEQUENCE: 6
```

| Met | Ser | Gln | Pro | Thr | Ile | Glu | Ser | Ile | Leu | Gln | Glu | Lys | Arg | Val | Phe |
|---|---|---|---|---|---|---|---|---|---|---|---|---|---|---|---|
| 1 | | | | 5 | | | | | 10 | | | | | 15 | |

| Pro | Pro | Ser | Ala | Glu | Phe | Ala | Ser | Ala | Ala | Arg | Ile | Asn | Pro | Glu | Ala |
|---|---|---|---|---|---|---|---|---|---|---|---|---|---|---|---|
| | | | 20 | | | | | 25 | | | | | 30 | | |

| Tyr | Glu | Ala | Leu | Cys | Gln | Lys | Ala | Ala | Ala | Asp | Pro | Val | Ala | Phe | Trp |
|---|---|---|---|---|---|---|---|---|---|---|---|---|---|---|---|
| | | | 35 | | | | | 40 | | | | | 45 | | |

| Gly | Glu | Leu | Ala | Ala | Gln | Glu | Leu | Asp | Trp | Phe | Glu | Pro | Trp | Gln | Gln |
|---|---|---|---|---|---|---|---|---|---|---|---|---|---|---|---|
| | 50 | | | | | 55 | | | | | 60 | | | | |

| Thr | Leu | Asp | Trp | Ser | Asn | Pro | Pro | Phe | Ala | Lys | Trp | Phe | Val | Gly | Gly |
|---|---|---|---|---|---|---|---|---|---|---|---|---|---|---|---|
| 65 | | | | | 70 | | | | | 75 | | | | | 80 |

| Lys | Leu | Asn | Ile | Ser | His | Asn | Cys | Leu | Asp | Arg | His | Leu | Thr | Thr | Trp |
|---|---|---|---|---|---|---|---|---|---|---|---|---|---|---|---|
| | | | | 85 | | | | | 90 | | | | | 95 | |

| Arg | Lys | Asn | Lys | Ala | Ala | Ile | Ile | Trp | Glu | Gly | Glu | Pro | Gly | Asp | Ser |
|---|---|---|---|---|---|---|---|---|---|---|---|---|---|---|---|
| | | | 100 | | | | | 105 | | | | | 110 | | |

| Arg | Thr | Leu | Thr | Tyr | Ala | Gln | Leu | His | Arg | Glu | Val | Cys | Gln | Phe | Ala |
|---|---|---|---|---|---|---|---|---|---|---|---|---|---|---|---|
| | | | 115 | | | | | 120 | | | | | 125 | | |

| Asn | Val | Leu | Lys | Ser | Leu | Gly | Ile | Gln | Lys | Gly | Asp | Val | Val | Gly | Val |
|---|---|---|---|---|---|---|---|---|---|---|---|---|---|---|---|
| | | | 130 | | | | | 135 | | | | | 140 | | |

| Tyr | Met | Pro | Met | Ile | Pro | Glu | Ala | Ala | Ile | Ala | Met | Leu | Ala | Cys | Ala |
|---|---|---|---|---|---|---|---|---|---|---|---|---|---|---|---|
| 145 | | | | | 150 | | | | | 155 | | | | | 160 |

| Arg | Ile | Gly | Ala | Val | His | Ser | Val | Val | Phe | Gly | Gly | Phe | Ser | Ala | Glu |
|---|---|---|---|---|---|---|---|---|---|---|---|---|---|---|---|
| | | | | 165 | | | | | 170 | | | | | 175 | |

| Ala | Leu | Arg | Asp | Arg | Leu | Val | Asp | Gly | Gln | Ala | Lys | Leu | Val | Val | Thr |
|---|---|---|---|---|---|---|---|---|---|---|---|---|---|---|---|
| | | | 180 | | | | | 185 | | | | | 190 | | |

| Ala | Asp | Gly | Gly | Trp | Arg | Lys | Asp | Ala | Ile | Val | Pro | Leu | Lys | Asp | Ser |
|---|---|---|---|---|---|---|---|---|---|---|---|---|---|---|---|
| | | | 195 | | | | | 200 | | | | | 205 | | |

| Val | Asp | Gln | Ala | Leu | Glu | Gly | Asn | Ala | Cys | Pro | Ser | Val | Gln | His | Val |
|---|---|---|---|---|---|---|---|---|---|---|---|---|---|---|---|
| | 210 | | | | | 215 | | | | | 220 | | | | |

| Leu | Val | Val | Glu | Arg | Thr | Lys | Gln | Asp | Ile | His | Met | Glu | Pro | Gly | Arg |
|---|---|---|---|---|---|---|---|---|---|---|---|---|---|---|---|
| 225 | | | | | 230 | | | | | 235 | | | | | 240 |

| Asp | His | Trp | Trp | His | Glu | Leu | Gln | Gln | Thr | Val | Ser | Ala | Thr | Cys | Pro |
|---|---|---|---|---|---|---|---|---|---|---|---|---|---|---|---|
| | | | | 245 | | | | | 250 | | | | | 255 | |

| Ala | Glu | Pro | Met | Asp | Ser | Glu | Asp | Leu | Leu | Phe | Val | Leu | Tyr | Thr | Ser |
|---|---|---|---|---|---|---|---|---|---|---|---|---|---|---|---|
| | | | 260 | | | | | 265 | | | | | 270 | | |

| Gly | Ser | Thr | Gly | Lys | Pro | Lys | Gly | Val | Val | His | Thr | Thr | Gly | Gly | Tyr |
|---|---|---|---|---|---|---|---|---|---|---|---|---|---|---|---|
| | | | 275 | | | | | 280 | | | | | 285 | | |

| Asn | Leu | Tyr | Ala | His | Ile | Thr | Thr | Gln | Trp | Thr | Phe | Asp | Leu | Gln | Asp |
|---|---|---|---|---|---|---|---|---|---|---|---|---|---|---|---|
| | 290 | | | | | 295 | | | | | 300 | | | | |

| Thr | Asp | Val | Tyr | Trp | Cys | Thr | Ala | Asp | Val | Gly | Trp | Ile | Thr | Gly | His |
|---|---|---|---|---|---|---|---|---|---|---|---|---|---|---|---|
| 305 | | | | | 310 | | | | | 315 | | | | | 320 |

| Ser | Tyr | Ile | Val | Tyr | Gly | Pro | Leu | Ser | Asn | Gly | Ala | Thr | Thr | Leu | Met |
|---|---|---|---|---|---|---|---|---|---|---|---|---|---|---|---|
| | | | | 325 | | | | | 330 | | | | | 335 | |

| Tyr | Glu | Gly | Ala | Pro | Arg | Ala | Ser | Asn | Pro | Gly | Cys | Phe | Trp | Asp | Val |
|---|---|---|---|---|---|---|---|---|---|---|---|---|---|---|---|

```
             340              345              350
Ile Glu Lys Tyr Gly Val Thr Thr Phe Tyr Thr Ala Pro Thr Ala Ile
            355              360              365

Arg Ala Phe Ile Lys Met Gly Glu Gln His Pro Ala Ala Arg Asp Leu
        370              375              380

Ser Ser Leu Arg Leu Leu Gly Thr Val Gly Glu Pro Ile Asn Pro Glu
385              390              395              400

Ala Trp Ile Trp Tyr His Arg Val Ile Gly Gly Asp Arg Cys Pro Ile
                405              410              415

Val Asp Thr Trp Trp Gln Thr Glu Thr Gly Gly His Met Ile Thr Ser
            420              425              430

Leu Pro Gly Ala Val Pro Thr Lys Pro Gly Ser Ala Thr Lys Pro Phe
        435              440              445

Pro Gly Ile Leu Ala Asp Val Val Asp Leu Asp Gly Arg Ser Val Pro
        450              455              460

Asp Asn Glu Gly Gly Tyr Leu Val Ile Arg His Pro Trp Pro Gly Met
465              470              475              480

Met Arg Thr Val Tyr Gly Asp Pro Asp Arg Phe Arg Arg Thr Tyr Trp
                485              490              495

Glu His Ile Pro Pro Gln Asn Gly Gln Tyr Leu Tyr Phe Ala Gly Asp
            500              505              510

Gly Ala Arg Arg Asp Ala Asp Gly Tyr Phe Trp Val Met Gly Arg Val
        515              520              525

Asp Asp Val Ile Asn Val Ser Gly His Arg Leu Gly Thr Met Glu Ile
        530              535              540

Glu Ser Ala Leu Val Ser His Pro Ala Val Ala Glu Ala Ala Val Val
545              550              555              560

Gly Arg Pro Asp Asp Leu Lys Gly Glu Gly Ile Val Ala Phe Ile Thr
                565              570              575

Leu Glu Ser Gly Ile Glu Thr Gly Asp Glu Leu Val Lys Asp Leu Lys
            580              585              590

Lys His Val Ala Gln Glu Ile Gly Ala Ile Ala Arg Pro Asp Glu Ile
        595              600              605

Arg Phe Ser Glu Ala Leu Pro Lys Thr Arg Ser Gly Lys Ile Met Arg
        610              615              620

Arg Leu Leu Arg Ser Leu Ala Ala Gly Gln Glu Val Ser Gly Asp Thr
625              630              635              640

Ser Thr Leu Glu Asp Arg Ser Val Leu Asp Lys Leu Arg Gln Gly Thr
                645              650              655

<210> SEQ ID NO 7
<211> LENGTH: 3898
<212> TYPE: DNA
<213> ORGANISM: Chloroflexus aurantiacus

<400> SEQUENCE: 7
aacatcatgg tatactatac ctatcgataa ttcttcaact aattgcataa cagaacagcg    60
atggcgacgg gggagtccat gagcggaaca ggacgactgg caggaaagat tgcgttaatt   120
accggtggcg ccggcaatat cggcagtgaa ttgacacgtc gctttctcgc agagggagcg   180
acggtcatta ttagtggacg gaatcgggcg aagttgaccg cactggccga acggatgcag   240
gcagaggcag gagtgccggc aaagcgcatc gatctcgaag tcatggatgg gagtgatccg   300
gtcgcggtac gtgccggtat cgaagcgatt gtggcccgtc acggccagat cgacattctg   360
gtcaacaatg caggaagtgc cggtgcccag cgtcgtctgg ccagattccc actcactgaa   420
```

```
gctgaattag gccctggcgc cgaagagacg cttcatgcca gcatcgccaa tttacttggt    480
atgggatggc atctgatgcg tattgcggca cctcatatgc cggtaggaag tgcggtcatc    540
aatgtctcga ccatctttc acgggctgag tactacgggc ggattccgta tgtcacccct     600
aaagctgctc ttaatgctct atctcaactt gctgcgcgtg agttaggtgc acgtggcatc    660
cgcgttaata cgatctttcc cggcccgatt gaaagtgatc gcatccgtac agtgttccag    720
cgtatggatc agctcaaggg gcggcccgaa ggcgacacag cgcaccattt tttgaacacc    780
atgcgattgt gtcgtgccaa cgaccagggc gcgcttgaac gtcggttccc ctccgtcggt    840
gatgtggcag acgccgctgt cttcctggcc agtgccgaat ccgccgctct ctccggtgag    900
acgattgagg ttacgcacgg aatggagttg ccggcctgca gtgagaccag cctgctggcc    960
cgtactgatc tgcgcacgat tgatgccagt ggccgcacga cgctcatctg cgccggcgac   1020
cagattgaag aggtgatggc gctcaccggt atgttgcgta cctgtgggag tgaagtgatc   1080
atcggcttcc gttcggctgc ggcgctgcc cagttcgagc aggcagtcaa tgagagtcgg    1140
cggctggccg gcgcagactt tacgcctccc attgccttgc cactcgatcc acgcgatccg   1200
gcaacaattg acgctgtctt cgattggggg gccggcgaga taccggcgg gattcatgca    1260 gcggtgattc tgcctgctac cagtcacgaa ccggcaccgt gcgtgattga ggttgatgat    1320
gagcgggtgc tgaattttct ggccgatgaa atcaccggga caattgtgat tgccagtcgc   1380
ctggcccgtt actggcagtc gcaacggctt acccccggcg cacgtgcgcg tgggccgcgt    1440 gtcattttc tctcgaacgg tgccgatcaa aatgggaatg tttacggacg cattcaaagt    1500
gccgctatcg gtcagctcat tcgtgtgtgg cgtcacgagg ctgaacttga ctatcagcgt    1560
gccagcgccg ccggtgatca tgtgctgccg ccggtatggg ccaatcagat tgtgcgcttc    1620
gctaaccgca gccttgaagg gttagaattt gcctgtgcct ggacagctca attgctccat    1680
agtcaacgcc atatcaatga gattaccctc aacatccctg ccaacattag cgccaccacc   1740
ggcgcacgca gtgcatcggt cggatgggcg gaaagcctga tcgggttgca tttggggaaa   1800
gttgccttga ttaccggtgg cagcgccggt attggtgggc agatcgggcg cctcctggct    1860
ttgagtggcg cgcgcgtgat gctggcagcc cgtgatcggc ataagctcga acagatgcag   1920
gcgatgatcc aatctgagct ggctgaggtg gggtataccg atgtcgaaga tcgcgtccac   1980
attgcaccgg gctgcgatgt gagtagcgaa gcgcagcttg cggatcttgt tgaacgtacc    2040
ctgtcagctt ttggcaccgt cgattatctg atcaacaacg ccgggatcgc cggtgtcgaa    2100
gagatggtta tcgatatgcc agttgaggga tggcgccata ccctcttcgc caatctgatc    2160
agcaactact cgttgatgcg caaactggcg ccgttgatga aaaaacaggg tagcggttac    2220
atccttaacg tctcatcata ctttggcggt gaaaagatg cggccattcc ctaccccaac     2280
cgtgccgatt acgccgtctc gaaggctggt cagcgggcaa tggccgaagt ctttgcgcgc    2340
ttccttggcc cggagataca gatcaatgcc attgcgccgg gtccggtcga aggtgatcgc    2400
ttgcgcggta ccggtgaacg tcccggcctc tttgcccgtc gggcgcggct gattttggag    2460
aacaagcggc tgaatgagct tcacgctgct cttatcgcgg ctgcgcgcac cgatgagcga    2520
tctatgcacg aactggttga actgctctta cccaatgatg tggccgcact agagcagaat    2580
cccgcagcac ctaccgcgtt gcgtgaactg gcacgacgtt ttcgcagcga aggcgatccg    2640
gcggcatcat caagcagtgc gctgctgaac cgttcaattg ccgctaaatt gctggctcgt    2700
ttgcataatg gtggctatgt gttgcctgcc gacatctttg caaacctgcc aaacccgccc    2760
gatcccttct tcacccgagc ccagattgat cgcgaggctc gcaaggttcg tgacggcatc    2820
```

```
atggggatgc tctacctgca acggatgccg actgagtttg atgtcgcaat ggccaccgtc   2880
tattaccttg ccgaccgcaa tgtcagtggt gagacattcc acccatcagg tggtttgcgt   2940
tacgaacgca cccctaccgg tggcgaactc ttcggcttgc cctcaccgga acggctggcg   3000
gagctggtcg gaagcacggt ctatctgata ggtgaacatc tgactgaaca ccttaacctg   3060
cttgcccgtg cgtacctcga acgttacggg gcacgtcagg tagtgatgat tgttgagaca   3120
gaaaccgggg cagagacaat gcgtcgcttg ctccacgatc acgtcgaggc tggtcggctg   3180
atgactattg tggccggtga tcagatcgaa gccgctatcg accaggctat cactcgctac   3240
ggtcgcccag gccggtcgt ctgtaccccc ttccggccac tgccgacggt accactggtc   3300
gggcgtaaag acagtgactg gagcacagtg ttgagtgagg ctgaatttgc cgagttgtgc   3360
gaacaccagc tcacccacca tttccgggta gcgcgcaaga ttgccctgag tgatggtgcc   3420
agtctcgcgc tggtcactcc cgaaactacg gctacctcaa ctaccgagca atttgctctg   3480
gctaacttca tcaaaacgac ccttcacgct tttacggcta cgattggtgt cgagagcgaa   3540
agaactgctc agcgcattct gatcaatcaa gtcgatctga cccggcgtgc gcgtgccgaa   3600
gagccgcgtg atccgcacga gcgtcaacaa gaactggaac gttttatcga ggcagtcttg   3660
ctggtcactg caccactccc gcctgaagcc gatacccgtt acgccgggcg gattcatcgc   3720
ggacgggcga ttaccgtgta aattctacgc cacaggaacc actaccaaac cagcatagta   3780
agagaacgat agagacgttg caatgcgacg tctctatcat atttccggcc ccccctagac   3840 aaaccccac gtcttcgtgt agactagaaa caggaggctg tatgcacgtc caacaaga    3898

<210> SEQ ID NO 8
<211> LENGTH: 1220
<212> TYPE: PRT
<213> ORGANISM: Chloroflexus aurantiacus

<400> SEQUENCE: 8

Met Ser Gly Thr Gly Arg Leu Ala Gly Lys Ile Ala Leu Ile Thr Gly
1               5                   10                  15

Gly Ala Gly Asn Ile Gly Ser Glu Leu Thr Arg Arg Phe Leu Ala Glu
            20                  25                  30

Gly Ala Thr Val Ile Ile Ser Gly Arg Asn Arg Ala Lys Leu Thr Ala
        35                  40                  45

Leu Ala Glu Arg Met Gln Ala Glu Ala Gly Val Pro Ala Lys Arg Ile
    50                  55                  60

Asp Leu Glu Val Met Asp Gly Ser Asp Pro Val Ala Val Arg Ala Gly
65                  70                  75                  80

Ile Glu Ala Ile Val Ala Arg His Gly Gln Ile Asp Ile Leu Val Asn
                85                  90                  95

Asn Ala Gly Ser Ala Gly Ala Gln Arg Arg Leu Ala Glu Ile Pro Leu
            100                 105                 110

Thr Glu Ala Glu Leu Gly Pro Gly Ala Glu Glu Thr Leu His Ala Ser
        115                 120                 125

Ile Ala Asn Leu Leu Gly Met Gly Trp His Leu Met Arg Ile Ala Ala
    130                 135                 140

Pro His Met Pro Val Gly Ser Ala Val Ile Asn Val Ser Thr Ile Phe
145                 150                 155                 160

Ser Arg Ala Glu Tyr Tyr Gly Arg Ile Pro Tyr Val Thr Pro Lys Ala
                165                 170                 175

Ala Leu Asn Ala Leu Ser Gln Leu Ala Ala Arg Glu Leu Gly Ala Arg
            180                 185                 190
```

```
Gly Ile Arg Val Asn Thr Ile Phe Pro Gly Pro Ile Glu Ser Asp Arg
            195                 200                 205
Ile Arg Thr Val Phe Gln Arg Met Asp Gln Leu Lys Gly Arg Pro Glu
        210                 215                 220
Gly Asp Thr Ala His His Phe Leu Asn Thr Met Arg Leu Cys Arg Ala
225                 230                 235                 240
Asn Asp Gln Gly Ala Leu Glu Arg Arg Phe Pro Ser Val Gly Asp Val
                245                 250                 255
Ala Asp Ala Ala Val Phe Leu Ala Ser Ala Glu Ser Ala Ala Leu Ser
            260                 265                 270
Gly Glu Thr Ile Glu Val Thr His Gly Met Glu Leu Pro Ala Cys Ser
        275                 280                 285
Glu Thr Ser Leu Leu Ala Arg Thr Asp Leu Arg Thr Ile Asp Ala Ser
    290                 295                 300
Gly Arg Thr Thr Leu Ile Cys Ala Gly Asp Gln Ile Glu Glu Val Met
305                 310                 315                 320
Ala Leu Thr Gly Met Leu Arg Thr Cys Gly Ser Glu Val Ile Ile Gly
                325                 330                 335
Phe Arg Ser Ala Ala Ala Leu Ala Gln Phe Glu Gln Ala Val Asn Glu
            340                 345                 350
Ser Arg Arg Leu Ala Gly Ala Asp Phe Thr Pro Pro Ile Ala Leu Pro
        355                 360                 365
Leu Asp Pro Arg Asp Pro Ala Thr Ile Asp Ala Val Phe Asp Trp Gly
    370                 375                 380
Ala Gly Glu Asn Thr Gly Gly Ile His Ala Ala Val Ile Leu Pro Ala
385                 390                 395                 400
Thr Ser His Glu Pro Ala Pro Cys Val Ile Glu Val Asp Asp Glu Arg
                405                 410                 415
Val Leu Asn Phe Leu Ala Asp Glu Ile Thr Gly Thr Ile Val Ile Ala
            420                 425                 430
Ser Arg Leu Ala Arg Tyr Trp Gln Ser Gln Arg Leu Thr Pro Gly Ala
        435                 440                 445
Arg Ala Arg Gly Pro Arg Val Ile Phe Leu Ser Asn Gly Ala Asp Gln
    450                 455                 460
Asn Gly Asn Val Tyr Gly Arg Ile Gln Ser Ala Ala Ile Gly Gln Leu
465                 470                 475                 480
Ile Arg Val Trp Arg His Glu Ala Glu Leu Asp Tyr Gln Arg Ala Ser
                485                 490                 495
Ala Ala Gly Asp His Val Leu Pro Pro Val Trp Ala Asn Gln Ile Val
            500                 505                 510
Arg Phe Ala Asn Arg Ser Leu Glu Gly Leu Glu Phe Ala Cys Ala Trp
        515                 520                 525
Thr Ala Gln Leu Leu His Ser Gln Arg His Ile Asn Glu Ile Thr Leu
    530                 535                 540
Asn Ile Pro Ala Asn Ile Ser Ala Thr Thr Gly Ala Arg Ser Ala Ser
545                 550                 555                 560
Val Gly Trp Ala Glu Ser Leu Ile Gly Leu His Leu Gly Lys Val Ala
                565                 570                 575
Leu Ile Thr Gly Gly Ser Ala Gly Ile Gly Gly Gln Ile Gly Arg Leu
            580                 585                 590
Leu Ala Leu Ser Gly Ala Arg Val Met Leu Ala Ala Arg Asp Arg His
        595                 600                 605
Lys Leu Glu Gln Met Gln Ala Met Ile Gln Ser Glu Leu Ala Glu Val
```

-continued

```
            610                 615                 620
Gly Tyr Thr Asp Val Glu Asp Arg Val His Ile Ala Pro Gly Cys Asp
625                 630                 635                 640

Val Ser Ser Glu Ala Gln Leu Ala Asp Leu Val Glu Arg Thr Leu Ser
                    645                 650                 655

Ala Phe Gly Thr Val Asp Tyr Leu Ile Asn Asn Ala Gly Ile Ala Gly
                    660                 665                 670

Val Glu Glu Met Val Ile Asp Met Pro Val Glu Gly Trp Arg His Thr
                    675                 680                 685

Leu Phe Ala Asn Leu Ile Ser Asn Tyr Ser Leu Met Arg Lys Leu Ala
                    690                 695                 700

Pro Leu Met Lys Lys Gln Gly Ser Gly Tyr Ile Leu Asn Val Ser Ser
705                 710                 715                 720

Tyr Phe Gly Gly Glu Lys Asp Ala Ala Ile Pro Tyr Pro Asn Arg Ala
                    725                 730                 735

Asp Tyr Ala Val Ser Lys Ala Gly Gln Arg Ala Met Ala Glu Val Phe
                    740                 745                 750

Ala Arg Phe Leu Gly Pro Glu Ile Gln Ile Asn Ala Ile Ala Pro Gly
                    755                 760                 765

Pro Val Glu Gly Asp Arg Leu Arg Gly Thr Gly Glu Arg Pro Gly Leu
770                 775                 780

Phe Ala Arg Arg Ala Arg Leu Ile Leu Glu Asn Lys Arg Leu Asn Glu
785                 790                 795                 800

Leu His Ala Ala Leu Ile Ala Ala Arg Thr Asp Glu Arg Ser Met
                    805                 810                 815

His Glu Leu Val Glu Leu Leu Pro Asn Asp Val Ala Ala Leu Glu
                    820                 825                 830

Gln Asn Pro Ala Ala Pro Thr Ala Leu Arg Glu Leu Ala Arg Arg Phe
                    835                 840                 845

Arg Ser Glu Gly Asp Pro Ala Ala Ser Ser Ser Ala Leu Leu Asn
850                 855                 860

Arg Ser Ile Ala Ala Lys Leu Leu Ala Arg Leu His Asn Gly Gly Tyr
865                 870                 875                 880

Val Leu Pro Ala Asp Ile Phe Ala Asn Leu Pro Asn Pro Pro Asp Pro
                    885                 890                 895

Phe Phe Thr Arg Ala Gln Ile Asp Arg Glu Ala Arg Lys Val Arg Asp
                    900                 905                 910

Gly Ile Met Gly Met Leu Tyr Leu Gln Arg Met Pro Thr Glu Phe Asp
                    915                 920                 925

Val Ala Met Ala Thr Val Tyr Tyr Leu Ala Asp Arg Asn Val Ser Gly
                    930                 935                 940

Glu Thr Phe His Pro Ser Gly Gly Leu Arg Tyr Glu Arg Thr Pro Thr
945                 950                 955                 960

Gly Gly Glu Leu Phe Gly Leu Pro Ser Pro Arg Leu Ala Glu Leu
                    965                 970                 975

Val Gly Ser Thr Val Tyr Leu Ile Gly Glu His Leu Thr Glu His Leu
                    980                 985                 990

Asn Leu Leu Ala Arg Ala Tyr Leu Glu Arg Tyr Gly Ala Arg Gln Val
                    995                 1000                1005

Val Met Ile Val Glu Thr Glu Thr Gly Ala Glu Thr Met Arg Arg
            1010                1015                1020

Leu Leu His Asp His Val Glu Ala Gly Arg Leu Met Thr Ile Val
            1025                1030                1035
```

```
Ala Gly Asp Gln Ile Glu Ala Ala Ile Asp Gln Ala Ile Thr Arg
    1040                1045                1050

Tyr Gly Arg Pro Gly Pro Val Val Cys Thr Pro Phe Arg Pro Leu
    1055                1060                1065

Pro Thr Val Pro Leu Val Gly Arg Lys Asp Ser Asp Trp Ser Thr
    1070                1075                1080

Val Leu Ser Glu Ala Glu Phe Ala Glu Leu Cys Glu His Gln Leu
    1085                1090                1095

Thr His His Phe Arg Val Ala Arg Lys Ile Ala Leu Ser Asp Gly
    1100                1105                1110

Ala Ser Leu Ala Leu Val Thr Pro Glu Thr Thr Ala Thr Ser Thr
    1115                1120                1125

Thr Glu Gln Phe Ala Leu Ala Asn Phe Ile Lys Thr Thr Leu His
    1130                1135                1140

Ala Phe Thr Ala Thr Ile Gly Val Glu Ser Glu Arg Thr Ala Gln
    1145                1150                1155

Arg Ile Leu Ile Asn Gln Val Asp Leu Thr Arg Arg Ala Arg Ala
    1160                1165                1170

Glu Glu Pro Arg Asp Pro His Glu Arg Gln Gln Glu Leu Glu Arg
    1175                1180                1185

Phe Ile Glu Ala Val Leu Leu Val Thr Ala Pro Leu Pro Pro Glu
    1190                1195                1200

Ala Asp Thr Arg Tyr Ala Gly Arg Ile His Arg Gly Arg Ala Ile
    1205                1210                1215

Thr Val
    1220

<210> SEQ ID NO 9
<211> LENGTH: 652
<212> TYPE: PRT
<213> ORGANISM: Escherichia coli

<400> SEQUENCE: 9

Met Ser Gln Ile His Lys His Thr Ile Pro Ala Asn Ile Ala Asp Arg
1               5                   10                  15

Cys Leu Ile Asn Pro Gln Gln Tyr Glu Ala Met Tyr Gln Gln Ser Ile
                20                  25                  30

Asn Val Pro Asp Thr Phe Trp Gly Glu Gln Gly Lys Ile Leu Asp Trp
            35                  40                  45

Ile Lys Pro Tyr Gln Lys Val Lys Asn Thr Ser Phe Ala Pro Gly Asn
        50                  55                  60

Val Ser Ile Lys Trp Tyr Glu Asp Gly Thr Leu Asn Leu Ala Ala Asn
65                  70                  75                  80

Cys Leu Asp Arg His Leu Gln Glu Asn Gly Asp Arg Thr Ala Ile Ile
                85                  90                  95

Trp Glu Gly Asp Asp Ala Ser Gln Ser Lys His Ile Ser Tyr Lys Glu
            100                 105                 110

Leu His Arg Asp Val Cys Arg Phe Ala Asn Thr Leu Leu Glu Leu Gly
        115                 120                 125

Ile Lys Lys Gly Asp Val Val Ala Ile Tyr Met Pro Met Val Pro Glu
    130                 135                 140

Ala Ala Val Ala Met Leu Ala Cys Ala Arg Ile Gly Ala Val His Ser
145                 150                 155                 160

Val Ile Phe Gly Gly Phe Ser Pro Glu Ala Val Ala Gly Arg Ile Ile
                165                 170                 175
```

-continued

```
Asp Ser Asn Ser Arg Leu Val Ile Thr Ser Asp Glu Gly Val Arg Ala
            180                 185                 190
Gly Arg Ser Ile Pro Leu Lys Lys Asn Val Asp Asp Ala Leu Lys Asn
        195                 200                 205
Pro Asn Val Thr Ser Val Glu His Val Val Leu Lys Arg Thr Gly
210                 215                 220
Gly Lys Ile Asp Trp Gln Glu Gly Arg Asp Leu Trp Trp His Asp Leu
225                 230                 235                 240
Val Glu Gln Ala Ser Asp Gln His Gln Ala Glu Met Asn Ala Glu
                245                 250                 255
Asp Pro Leu Phe Ile Leu Tyr Thr Ser Gly Ser Thr Gly Lys Pro Lys
            260                 265                 270
Gly Val Leu His Thr Thr Gly Gly Tyr Leu Val Tyr Ala Ala Leu Thr
        275                 280                 285
Phe Lys Tyr Val Phe Asp Tyr His Pro Gly Asp Ile Tyr Trp Cys Thr
    290                 295                 300
Ala Asp Val Gly Trp Val Thr Gly His Ser Tyr Leu Leu Tyr Gly Pro
305                 310                 315                 320
Leu Ala Cys Gly Ala Thr Thr Leu Met Phe Glu Gly Val Pro Asn Trp
                325                 330                 335
Pro Thr Pro Ala Arg Met Ala Gln Val Val Asp Lys His Gln Val Asn
            340                 345                 350
Ile Leu Tyr Thr Ala Pro Thr Ala Ile Arg Ala Leu Met Ala Glu Gly
        355                 360                 365
Asp Lys Ala Ile Glu Gly Thr Asp Arg Ser Ser Leu Arg Ile Leu Gly
    370                 375                 380
Ser Val Gly Glu Pro Ile Asn Pro Glu Ala Trp Glu Trp Tyr Trp Lys
385                 390                 395                 400
Lys Ile Gly Asn Glu Lys Cys Pro Val Val Asp Thr Trp Trp Gln Thr
                405                 410                 415
Glu Thr Gly Gly Phe Met Ile Thr Pro Leu Pro Gly Ala Thr Glu Leu
            420                 425                 430
Lys Ala Gly Ser Ala Thr Arg Pro Phe Phe Gly Val Gln Pro Ala Leu
        435                 440                 445
Val Asp Asn Glu Gly Asn Pro Leu Glu Gly Ala Thr Glu Gly Ser Leu
    450                 455                 460
Val Ile Thr Asp Ser Trp Pro Gly Gln Ala Arg Thr Leu Phe Gly Asp
465                 470                 475                 480
His Glu Arg Phe Glu Gln Thr Tyr Phe Ser Thr Phe Lys Asn Met Tyr
                485                 490                 495
Phe Ser Gly Asp Gly Ala Arg Arg Asp Glu Asp Gly Tyr Tyr Trp Ile
            500                 505                 510
Thr Gly Arg Val Asp Asp Val Leu Asn Val Ser Gly His Arg Leu Gly
        515                 520                 525
Thr Ala Glu Ile Glu Ser Ala Leu Val Ala His Pro Lys Ile Ala Glu
    530                 535                 540
Ala Ala Val Val Gly Ile Pro His Asn Ile Lys Gly Gln Ala Ile Tyr
545                 550                 555                 560
Ala Tyr Val Thr Leu Asn His Gly Glu Glu Pro Ser Pro Glu Leu Tyr
                565                 570                 575
Ala Glu Val Arg Asn Trp Val Arg Lys Glu Ile Gly Pro Leu Ala Thr
            580                 585                 590
Pro Asp Val Leu His Trp Thr Asp Ser Leu Pro Lys Thr Arg Ser Gly
        595                 600                 605
```

```
Lys Ile Met Arg Arg Ile Leu Arg Lys Ile Ala Ala Gly Asp Thr Ser
    610                 615                 620

Asn Leu Gly Asp Thr Ser Thr Leu Ala Asp Pro Gly Val Val Glu Lys
625                 630                 635                 640

Leu Leu Glu Glu Lys Gln Ala Ile Ala Met Pro Ser
                645                 650

<210> SEQ ID NO 10
<211> LENGTH: 645
<212> TYPE: PRT
<213> ORGANISM: Pseudomonas fulva

<400> SEQUENCE: 10

Met Ser Leu Pro His Arg Tyr Pro Val Ser Asp Ala Ala Arg Gln Arg
1               5                   10                  15

Thr His Leu Asp Asp Thr Ala Tyr Gln Arg Leu Tyr Arg Gln Ser Val
            20                  25                  30

Asp Asp Pro Gln Thr Phe Trp Gly Glu Gln Ala Lys Ala Phe Leu Asp
        35                  40                  45

Trp Phe Lys Pro Trp Asp Glu Val Cys Ser Gly Ser Leu Ser Lys Gly
    50                  55                  60

Asp Ile Arg Trp Phe Ser Gly Gly Gln Leu Asn Ile Ser His Asn Cys
65                  70                  75                  80

Ile Asp Arg His Leu Ala Lys Arg Gly Asp Gln Val Ala Leu Ile Trp
                85                  90                  95

Glu Gly Asp Asp Pro Met Asp Ser Ala Arg Ile Thr Tyr Arg Glu Leu
            100                 105                 110

His Glu Gln Val Cys Arg Leu Ala Asn Val Leu Lys Ser Arg Gly Val
        115                 120                 125

Lys Lys Gly Asp Arg Val Cys Ile Tyr Met Pro Met Val Pro Gln Ala
    130                 135                 140

Ala Tyr Ala Met Leu Ala Cys Thr Arg Ile Gly Ala Val His Ser Val
145                 150                 155                 160

Val Phe Gly Gly Phe Ser Pro Asp Ala Leu Arg Asp Arg Ile Leu Asp
                165                 170                 175

Ala Asp Cys Arg Thr Val Ile Thr Ala Asp Glu Ala Val Arg Gly Gly
            180                 185                 190

Lys Leu Ile Pro Leu Lys Ser Asn Val Asp Lys Ala Leu Ala Ser Cys
        195                 200                 205

Pro Asn Val Ser Thr Val Leu Val Val Lys Arg Thr Gly Asn Lys Val
    210                 215                 220

Asp Trp Asp Asp Lys Arg Asp Leu Trp Tyr Ala Glu Ala Val Gln Gln
225                 230                 235                 240

Ala Gly Ala Asp Cys Pro Ala Glu Pro Met Asp Ala Glu Asp Pro Leu
                245                 250                 255

Phe Ile Leu Tyr Thr Ser Gly Ser Thr Gly Lys Pro Lys Gly Val Leu
            260                 265                 270

His Ser Thr Ala Gly Tyr Leu Leu Gln Ala Ala Met Thr His Lys Tyr
        275                 280                 285

Val Phe Asp Tyr His Asp Gly Asp Ile Tyr Trp Cys Thr Ala Asp Val
    290                 295                 300

Gly Trp Val Thr Gly His Ser Tyr Ile Val Tyr Gly Pro Leu Ala Asn
305                 310                 315                 320

Gly Ala Thr Ser Leu Ile Phe Glu Gly Val Pro Asn Tyr Pro Asp Thr
                325                 330                 335
```

-continued

```
Ser Arg Phe Trp Gln Val Ile Asp Lys His Gln Val Asn Ile Phe Tyr
                340             345             350

Thr Ala Pro Thr Ala Leu Arg Ala Leu Met Arg Glu Gly Glu Ala Pro
        355             360             365

Val Lys Lys Ala Ser Arg Ser Ser Leu Arg Leu Leu Gly Ser Val Gly
        370             375             380

Glu Pro Ile Asn Pro Glu Ala Trp Glu Trp Tyr Phe Lys Val Val Gly
385             390             395             400

Glu Gln Arg Cys Pro Ile Val Asp Thr Trp Trp Gln Thr Glu Thr Gly
                405             410             415

Ala Ile Met Ile Thr Pro Leu Pro Gly Ala Thr Asp Leu Lys Pro Gly
                420             425             430

Ser Ala Thr Arg Pro Phe Phe Gly Val Gln Pro Val Leu Leu Asp Glu
        435             440             445

Gln Gly Lys Glu Ile Asp Gly Pro Gly Ala Gly Val Leu Ala Ile Lys
        450             455             460

Ala Ser Trp Pro Ser Gln Ile Arg Ser Val Tyr Gly Asp His Lys Arg
465             470             475             480

Met Leu Glu Thr Tyr Phe Thr Ala Tyr Pro Gly Tyr Tyr Phe Ser Gly
                485             490             495

Asp Gly Ala Arg Arg Asp Glu Asp Gly Tyr Trp Trp Ile Thr Gly Arg
                500             505             510

Ile Asp Asp Val Ile Asn Val Ser Gly His Arg Ile Gly Thr Ala Glu
        515             520             525

Val Glu Ser Ala Leu Val Leu His Asp Ala Val Ala Glu Ala Ala Val
        530             535             540

Val Gly Tyr Pro His Asp Val Lys Gly Gln Gly Ile Tyr Ala Phe Val
545             550             555             560

Thr Thr Met Asn Gly Val Glu Pro Ser Asp Glu Leu Lys Lys Glu Leu
                565             570             575

Leu Ser Leu Val Gly Lys Glu Ile Gly Asn Phe Ala Lys Pro Glu Leu
        580             585             590

Ile Gln Trp Ala Pro Gly Leu Pro Lys Thr Arg Ser Gly Lys Ile Met
        595             600             605

Arg Arg Ile Leu Arg Lys Ile Ala Cys Asn Glu Leu Asp Ser Leu Gly
        610             615             620

Asp Thr Ser Thr Leu Ala Asp Pro Ser Val Val Asp Ser Leu Ile Glu
625             630             635             640

Gln Arg Val Asn Asn
                645
```